United States Patent [19]

Amano

[11] Patent Number: 5,704,363
[45] Date of Patent: Jan. 6, 1998

[54] PRESSURE SENSOR, PRESSURE FLUCTUATION DETECTOR AND PULSE DETECTOR USING THE PRESSURE SENSOR

[75] Inventor: Kazuhiko Amano, Suwa, Japan

[73] Assignee: Seiko Epson Corporation, Tokyo, Japan

[21] Appl. No.: 403,697

[22] PCT Filed: Aug. 11, 1994

[86] PCT No.: PCT/JP94/01328

§ 371 Date: May 15, 1995

§ 102(e) Date: May 15, 1995

[87] PCT Pub. No.: WO95/04919

PCT Pub. Date: Feb. 16, 1995

[30] Foreign Application Priority Data

Aug. 11, 1993 [JP] Japan ................. 5-199821
Jan. 31, 1994 [JP] Japan ................. 6-010144

[51] Int. Cl.$^6$ ............................................ A61B 5/02
[52] U.S. Cl. ........................................... 128/687
[58] Field of Search ........................... 128/672, 675, 128/687–690

[56] References Cited

U.S. PATENT DOCUMENTS

| | | | |
|---|---|---|---|
| 3,535,067 | 10/1970 | Lesher et al. ................. | 128/690 |
| 4,802,488 | 2/1989 | Eckerle ........................ | 128/690 |
| 5,131,400 | 7/1992 | Harada et al. . | |
| 5,381,797 | 1/1995 | Pak et al. ..................... | 128/688 |

FOREIGN PATENT DOCUMENTS

| | | |
|---|---|---|
| 1-259836 | 10/1989 | Japan . |
| 2-212729 | 8/1990 | Japan . |
| 2-246861 | 2/1992 | Japan . |
| 5-31085 | 2/1993 | Japan . |
| 5-300886 | 11/1993 | Japan . |
| 2-240399 | 7/1991 | United Kingdom . |

*Primary Examiner*—Jennifer Bahr
*Assistant Examiner*—Samuel Gilbert
*Attorney, Agent, or Firm*—Mark P. Watson

[57] ABSTRACT

The present invention has as its objective the presentation of a compact and simple pressure sensor having the ability to measure pulses, the pressure sensor 10 being composed of pressure sensing elements $S_1-S_4$ and elastic rubber body 1. The measurement positions $Q_1-Q_4$ of the pressure sensing elements $S_1-S_4$ are on the bottom surface L of the convex-shaped elastic rubber body 1, at the same distance a from the origin of the x and y axes. If the elastic rubber body 1 is pressed in the vicinity of an artery, blood current changes in said artery, that is, vibrations from the artery occur on the exposed surface of the elastic rubber body 1, these vibrations propagate through the elastic rubber body 1 as elastic waves, and are measured as pressure waves by the pressure sensing elements $S_1-S_4$. Their magnitudes decrease as the inverse square of the propagation distance of the elastic waves through the elastic rubber body 1, and the coordinates of the projection of the pressure wave generation point on the bottom surface L are calculated from the voltages $V_1-V_4$ of the pressure sensing elements $S_1-S_4$ and the distances from the pressure vibration generation point to the measurement positions $Q_1-Q_4$. By determining these coordinates for each passage of a set time interval, the pulse front propagation speed and the artery position are able to be determined.

33 Claims, 13 Drawing Sheets

FIG.4A CONTROL SIGNAL T
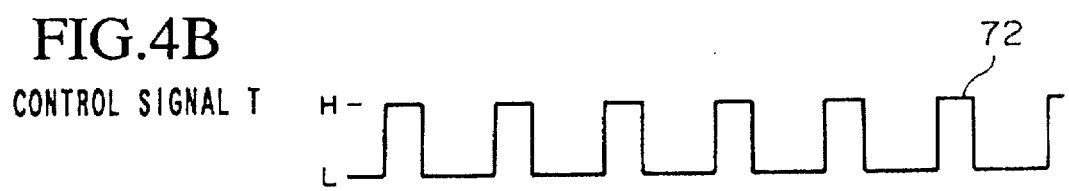
FIG.4B CONTROL SIGNAL T
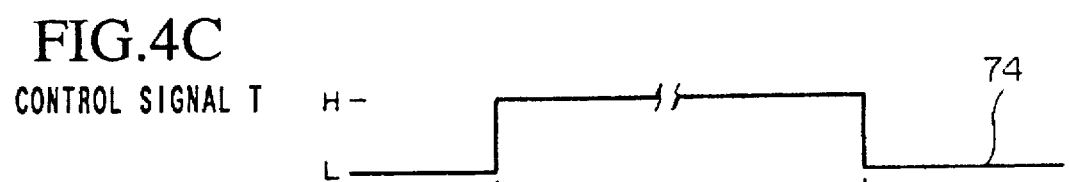
FIG.4C CONTROL SIGNAL T
NO MEASUREMENT | MEASUREMENT | NO MEASUREMENT
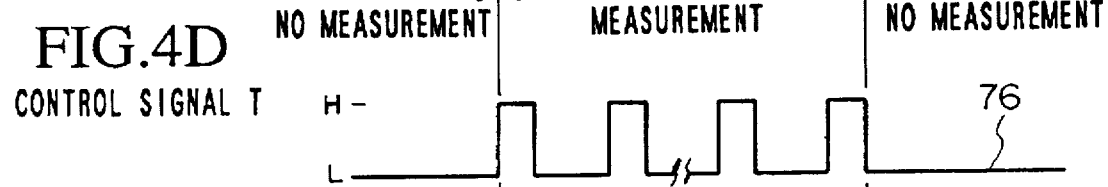
FIG.4D CONTROL SIGNAL T
FIG.4E BIAS
FIG.4F BIAS

PRESSURE SENSOR, PRESSURE FLUCTUATION DETECTOR AND PULSE DETECTOR USING THE PRESSURE SENSOR

BACKGROUND OF THE INVENTION

1. Field of the Invention

The present invention relates to a pressure sensor suitable for detecting pulses by installation in a wristwatch, a pressure vibration detector for detecting pressure vibrations using said pressure sensor, and a pulse detector for detecting a patient's pulse using said pressure sensor.

2. Description of the Related Art

The word "pulse" refers to the waves of blood which has been pumped out from the heart and propagates through the blood vessels, and it is known that by detecting these pulses and analyzing them, it is possible to obtain various types of medical information. For example, a patient's physical/psychological information may be obtained from the mathematical parameters (such as the maximum point, minimum point, or points of inflection) of the pulse waveform, furthermore, a blood pressure value having a positive correlation (a proportional relationship) with the propagation speed may be determined.

As sensors for detecting these types of pulses, in the past, there were in principle two forms. That is, (1) a form in which a patient's fingertip was irradiated with infrared light, and the amount of reflection of said infrared light (due to blood) was measured, and (2) a form in which a pressure sensor was placed so as to apply pressure to a patient's artery, for example the radial artery, and a measurement signal was obtained.

Form (1) works by placing an infrared light emitting diode and a photosensor in the appropriate light emitting and detection directions.

In recent years, the demand for the ability to diagnose, simply and accurately, as well as continuously, one's physical and psychological condition based on one's detected pulse, has been increasing.

In order to meet this demand, one can conceive of prodding a sensor for detecting pulses in an object, such as a wristwatch, which the patient holds during everyday activity, and adding a function to diagnose his physical and psychological condition from the detected pulse.

However, in providing a sensor on a wristwatch, and measuring a pulse using the above forms (1) and (2), the following problems existed. That is, (1) In the form in which the amount of infrared reflection of blood was detected, a region needed to be provided on the surface of the watch case for allowing contact of the patient's fingertip. On the surface of the watch case, a display section is normally provided, and it is difficult to provide a region for detecting pulses in the limited space on a wristwatch, so there was a problem in that it introduced a severe restriction on the outward design of the wristwatch.

(2) Furthermore, in the case of using a common pressure sensor of the prior art, the measurement region of said sensor and the radial artery must come into contact. The style of wearing wristwatches differs with the user, and the variation in the position of the radial artery is also large. Therefore, there was the problem that it was difficult to align the measurement region of the pressure sensor with everybody's radial artery.

SUMMARY OF THE INVENTION

Consequently, the objective of the present invention is to offer a new type of pressure sensor with which it is possible to detect pulses, as well as to offer a pressure vibration detector using this pressure sensor and a pulse detector in which this pressure vibration detector is applied, and which solves the above problems in addition to having almost no effect on the outward design of wristwatches.

Therefore, Invention 1 is characterized in that it measures the various pressures at different positions on a flat surface, is provided with at least three pressure measurement means for outputting signals based on the pressures at each position, and an elastic member which attaches to the aforementioned flat surface, being convex in shape, such that the bottom surfaces cover the measurement positions of the aforementioned at least three pressure measurement means, and by pressing the exposed surface of the aforementioned elastic member in the direction of the surface of measurement, the pressure vibrations on the aforementioned surface of measurement are detected. With this invention, if pressure vibrations are generated on the exposed surface of the elastic member, said pressure vibrations propagate through the elastic member as elastic waves, becoming dampened as the inverse square of the propagation distance, and are converted into signals describing said pressure vibrations by the respective pressure measurement means. Therefore, it is possible to detect the pressure as an electrical signal.

Invention 2 is characterized in that, given Invention 1, the aforementioned elastic member and the aforementioned at least three pressure measurement means are attached by an elastic adhesive layer. With this invention, minute vibrations in the elastic member are able to be prevented from directly contacting the pressure measurement means, and the accuracy of the measurement is increased.

Invention 3 is characterized in that, given Invention 1, it has four of the aforementioned at least three pressure measurement means, and the positions of measurement are on mutually orthogonal axes to the centers of the bottom surface of the respective elastic member, at equal distances from the aforementioned centers of the bottom surfaces. With this invention, the positions of pressure measurement are distributed symmetrically with respect to the center of the bottom surface of the elastic member. As a result, even if the point of generation of the pressure vibrations moves, the dampening effect of the elastic member may be equalized with respect to each pressure measurement means. Furthermore, if the direction of movement of the pressure vibration point passes through the highest point on the elastic member, and is aligned with one of the axes of the measurement positions, then the transmitted distance of the elastic waves is minimized, and it becomes possible to make a more accurate pressure measurement.

Invention 4 is characterized in that, given Invention 1, the aforementioned at least three pressure measurement means are each formed on the same semi-conductor substrate. With this invention, it is possible to utilize semi-conductor manufacturing technology, making possible extremely small-scale and precise manufacturing.

Invention 5 is characterized in that, given Invention 4, underneath the bottom surface of the aforementioned elastic member, hollow chambers are provided opening onto the various positions on the aforementioned surface, the aforementioned at least three pressure measurement means are each stored in a corresponding hollow chamber, and the interior pressures of said hollow chambers are measured.

Invention 6 is characterized in that, given Invention 5, the aforementioned hollow chambers are filled with a liquid. With these Inventions 5 and 6, similar to the second invention, minute vibrations in the elastic member are able to be prevented from directly contacting the pressure measurement means, and the accuracy of the measurement is increased.

Invention 7 is characterized in that, given Invention 4, underneath the bottom surface of the aforementioned elastic member, hollow chambers opening onto the various positions on the aforementioned surface and pressure transmission routes connecting the respective interior pressures of the aforementioned hollow chambers to the aforementioned at least three pressure measurement means are provided, and each of the aforementioned at least three pressure measurement means measures the interior pressure of the corresponding pressure transmission route.

Invention 8 is characterized in that, given Invention 7, the aforementioned hollow chambers and the aforementioned pressure transmission routes are filled with a liquid.

Invention 9 is characterized in that, given Invention 7, the aforementioned pressure transmission route is comprised of a rigid body. With these Inventions 7–9, it is possible to place the pressure measurement means without regard to the position at which the pressure should be measured. Specifically, if the pressure transmission routes are provided so as to point towards the center of the surface, then the pressure measurement means may be concentrated, and a number of pressure measurement means may be formed on a unit of surface area on the semi-conductor substrate, thus contributing to cost reduction.

Invention 10 is characterized in that, given Invention 1, a highly elastic member having an elasticity higher than the aforementioned elastic member is coated on the exposed surface of the aforementioned elastic member. With this invention, by coating with a highly elastic material, surface elastic waves propagating along the exposed surface are reduced, and the elastic waves traveling in the direction of measurement become that much larger, so it is possible to make the level of the signal output from the pressure measurement means larger.

Invention 11 is characterized in that, given Invention 1, parts composed of a highly elastic material having an elasticity higher than the aforementioned coating material are dispersed on the exposed surface of the aforementioned elastic member. With this invention, the generation of vibrations on the exposed surface of the elastic member becomes dispersive, but because the surface elastic waves propagating along the exposed surface may be diminished by the addition of highly elastic materials, the elastic waves propagating in the direction of measurement may be made larger, and thus the level of the signal output from each pressure measurement means can be increased.

Invention 12 is characterized in that, given Invention 1, each of the aforementioned at least three pressure measurement means outputs signals depending on the pressure based on a set bias signal, and it is provided with a bias signal means for setting an equal bias signal on each of the aforementioned at least three pressure measurement means. With this invention, because of the equal bias signal, it is possible to compare the signals output from the aforementioned at least three pressure measurement means under the same conditions.

Invention 13 is characterized in that, given Invention 12, the aforementioned bias signal means sets a bias signal for each of the aforementioned at least three pressure measurement means only when a pressure is being measured.

Invention 14 is characterized in that, given Invention 12, the aforementioned bias signal means sets a bias signal for each of the aforementioned at least three pressure measurement means one at a time.

Invention 15 is characterized in that, given Invention 12, the aforementioned bias is a constant current pulse. With these Inventions 13–15, the operation of each pressure measurement means becomes intermittent, and compared with always setting a bias signal for each pressure measurement means, the usage of electricity is decreased during the pressure measurement.

Invention 16 is characterized in that, given Invention 12, a converter means is further provided for converting the output signals of the aforementioned at least three pressure measurement means into digital signals.

Invention 17 is characterized in that, given Invention 16, the aforementioned converter means performs a digital conversion while the aforementioned bias signal means is setting a bias signal for the aforementioned at least three pressure measurement means.

Invention 18 is characterized in that, given Invention 16, a memory means is further provided for storing in order at least one of the digital signals converted by the aforementioned converter means. With these Inventions 16–18, the output signals from the aforementioned at least three pressure measurement means are efficiently converted to digital signals, and therefore various digital procedures are possible.

Invention 19 is characterized in that, given Invention 16, the surface of measurement is a patient's skin, and a pulse from an artery positioned in the vicinity of the place where the aforementioned elastic member is pressed is detected as a pressure vibration by at least one of the aforementioned at least three pressure measurement means. With this invention, when the exposed surface of the elastic member is pressed against the patient, a pressure vibration is generated on the exposed surface of the elastic member by a pulse positioned in the vicinity of the place where it has been pressed. Pressure vibrations due to pulses propagate through the elastic member as elastic waves, being dampened as the inverse square of the propagation distance, and are converted to signals which represent the pulse by the respective pressure measurement means. With this, it is possible to measure a patient's pulse.

Invention 20 is characterized in that, given Invention 19, the aforementioned elastic member is attached to a patient by a strap which is wound around the patient's wrist.

Invention 21 is characterized in that, given Invention 19, the artery in the vicinity of the place where the aforementioned elastic member is pressed is the radial artery. With these Inventions 20 and 21, the pressure sensor is always wound around the patient's wrist, so it is possible to constantly measure the pulse.

Invention 22 is characterized in that, given Invention 19, a mathematical coordinate calculation means is further provided for determining the mathematical coordinates for a waveform of a pulse wave detected by at least one of the aforementioned at least three pressure measurement means. With this invention, by determining the mathematical coordinates of the pulse waveform, it is possible to collect data necessary for obtaining the patient's physical condition.

Invention 23 is characterized in that, given Invention 22, a discrimination means is further provided for discriminating the patient's physical condition based on the mathematical coordinates determined by the aforementioned mathematical coordinate calculation means.

Invention 24 is characterized in that, given Invention 23, a first display means is further provided displaying the physical condition of the patient discriminated by the aforementioned discrimination means. With these Inventions 23 and 24, it is possible to show the patient's physical condition to the patient himself.

Invention 25 is characterized in that, given Invention 22, if the aforementioned mathematical coordinate calculation means detects a minimum value for the pulse waveform and a third maximum after the aforementioned minimum value, then the pulse waveform mathematical coordinate calculation means outputs a signal indicating this. With this invention, it is possible to determine the time period necessary for obtaining the patient's physical condition.

Invention 26 is characterized in that, given Invention 19, it is further provided with a first calculation means for determining, with each passing of a set period of time, the coordinates of the pressure vibration point generated on the exposed surface of the aforementioned elastic member by the pulse from the artery positioned in the vicinity of the place where the aforementioned elastic member has been pressed, projected onto the aforementioned flat surface, from the ratios of the respective measurement signals from the aforementioned at least three pressure measurement means, and a second calculation means for determining the shift speed of the coordinates determined by the aforementioned first calculation means with each passing of a set period of time, and outputs said shift speed as the pulse wave propagation speed of the relevant artery. With this invention, when the exposed surface of the elastic member is pressed onto a patient, a pressure vibration is generated on the exposed surface of the elastic member by the pulse from the artery positioned in the vicinity of the place where it is pressed. This pressure vibration shifts with the propagation of the pulse front, so by determining the coordinates of the pressure vibration point on the exposed surface projected onto a flat surface by the first calculation means with each passing of a set period of time, and calculating the shift speed of the determined coordinates by the second calculation means, the propagation speed of the pulse front is able to be determined.

Invention 27 is characterized in that, given Invention 26, it is further provided with a first time interval control means for determining the magnitude of the aforementioned shift speed, and changing the length of the aforementioned set time period. With this invention, because the interval for determining the coordinates from the first calculation means changes with the shift speed of the coordinates, it is possible to efficiently calculate the coordinates.

Invention 28 is characterized in that, given Invention 26, it is further provided with a second memory means for pre-storing the correlation between the pulse front propagation speed and the normal blood pressure value, a setting means for setting the patient's personal data, and a blood pressure value calculation means for reading the normal blood pressure value associated with the output pulse front propagation speed, accounting for the set personal data, and outputting the patient's blood pressure value.

Invention 29 is characterized in that, given Invention 28, it is further provided with a second display means for displaying the patient's blood pressure information output from the aforementioned blood pressure value calculation means. With these Inventions 28 and 29, it is possible to obtain the patient's blood pressure information from the determined pulse front propagation speed.

Invention 30 is characterized in that, given Invention 19, it is further provided with a first calculation means for determining, with each passing of a set period of time, the coordinates of the pressure vibration point generated on the exposed surface of the aforementioned elastic member by the pulse from the artery positioned in the vicinity of the place where the aforementioned elastic member has been pressed, projected onto the aforementioned flat surface, from the ratios of the respective measurement signals from the aforementioned at least three pressure measurement means, and a third display means for plotting and displaying the coordinates determined with each passing of a set period of time by the aforementioned first calculation means. With this invention, when the exposed surface of the elastic member is pressed onto the patient, a pressure vibration is generated on the exposed surface of the elastic member by the pulse from the artery positioned in the vicinity of the place where it is pressed. This pressure vibration shifts with the propagation of the pulse front, so by determining the coordinates of the pressure vibration point on the exposed surface projected onto a flat surface by the first calculation means with each passing of a set period of time, and plotting and displaying the determined coordinates by the display means, it is possible to display the artery position.

Invention 31 is characterized in that, given Invention 30, it is further provided with a second time interval control means for discriminating the magnitude of the shift speed of the aforementioned coordinates, and changing the length of the aforementioned set period of time. With this invention, the interval for determining the coordinates is changed according to the shift speed of the coordinates, so it is possible to precisely display the position of the artery.

Invention 32 is characterized in that, given Invention 30, the aforementioned third display means compares and displays the measurement positions of the aforementioned at least three pressure measurement means and the coordinates determined from the aforementioned first calculation means. With this invention, the deviation between the pressure measurement position and the arterial position is displayed, making it possible to know the best position for measuring pulses.

Invention 33 is characterized in that, given Invention 1, a dome-shaped cavity is provided in the aforementioned elastic member in a position covering the position of measurement of the aforementioned pressure measurement means.

In addition, Invention 34 is characterized in that, given Invention 33, the aforementioned dome-shaped cavity, having a bottom diameter s, is provided in the aforementioned elastic member, having a bottom radius r, so as to satisfy the following relationship:

$$\frac{4}{5} \geq \frac{s}{r} \geq \frac{1}{5}$$

With these Inventions 33 and 34, because the volume of the space formed by the dome-shaped cavity is easily changeable due to pressure applied to the elastic member, the pressure measurement means is able to more easily detect the pressure, and as a result the sensitivity of the pressure measurement means is increased.

Other objects and attainments together with a fuller understanding of the invention will become apparent and appreciated by referring to the following description and claims taken in conjunction with the accompanying drawings.

BRIEF DESCRIPTION OF THE DRAWINGS

FIGS. 4A–4F are timing diagrams showing examples of the control signal T of the bias circuit 60, and FIGS. 4E–4F are diagrams showing the waveforms of the constant current pulse from bias circuit 60.

DESCRIPTION OF THE PREFERRED EMBODIMENTS

Below, the various embodiments of the present invention will be explained with reference to the drawings.

A: Pressure Sensor

The pressure sensor according to this invention senses pressure vibrations and also calculates the coordinates of the point of generation of these pressure vibrations. In this embodiment, the detection of these pressure vibrations will be explained with the measurement of a patient's arterial pulse (especially the radial artery) as an example, additionally, the measurement of the pulse front propagation speed and the position display of the patient's artery (in this case the radial artery) will be explained.

Figure 1A:
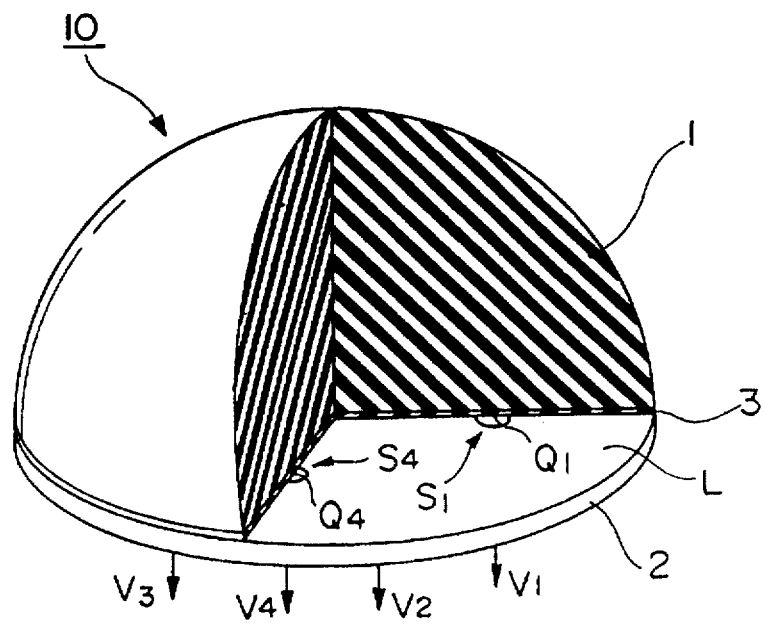
FIG. 1A is a partly cutaway oblique view diagram showing the composition of pressure sensor 10 according to Embodiment 1 of the present invention.
Figure 1B:
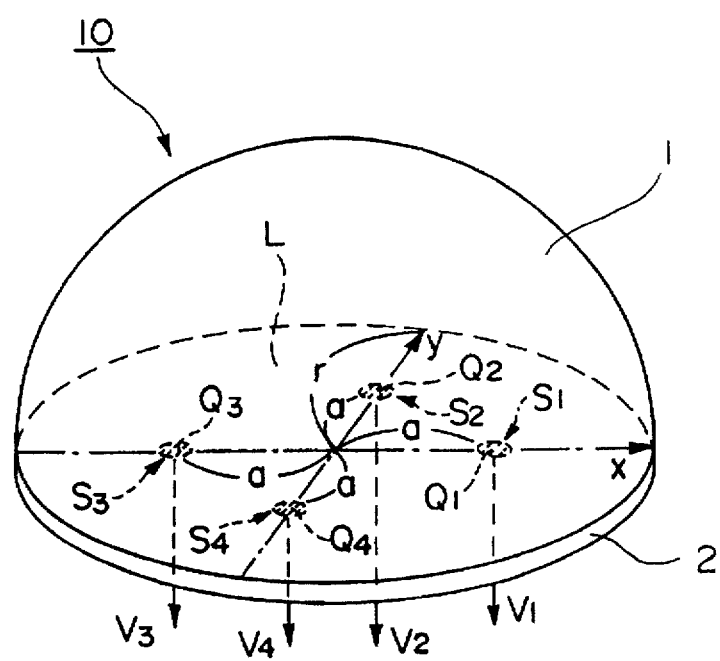
FIG. 1B is a transparent oblique view diagram showing the same composition.

FIGS. 1A and 1B respectively show the composition of the pressure sensor according to this embodiment in an oblique view of a partial cutaway diagrams and an oblique view of a transparent diagram.

As shown in these diagrams, the pressure sensor 10 is composed of pressure sensing elements $S_1-S_4$ and a hemispherical elastic rubber body 1. Here, the shape of the elastic rubber body 1 will be taken as a perfect hemisphere.

The respective pressure sensing elements $S_1-S_4$ are provided on the bottom surface (flat surface) of the elastic rubber body 1, output respective measurement signals of voltage $V_1-V_4$ proportional to the detected pressures, and their compositions will be explained later. The coordinates $(x, y)$ of the measurement positions $Q_1-Q_4$ of the pressure sensing elements $S_1-S_4$, taking the radius of the elastic rubber body as r and the center of the bottom surface L as the origin (0, 0), are respectively $$(a, 0), (0, a), (-a, 0), (0, -a) \qquad (p)$$

(provided that $r > a > 0$)

Therefore, the coordinates at which the pressures should be measured by the pressure sensing elements $S_1-S_4$ are on the x and y axes of the bottom surface L, and are each located at an equal distance a from the origin.

Next, the connecting portion between the pressure sensing elements and the elastic rubber body 1 will be explained with the pressure sensing element $S_1$ as an example.

On the bottom surface L of the elastic rubber body, the semi-conductor substrate 2 is attached by an adhesive layer 3 having elasticity, and in said semi-conductor substrate 2, the pressure sensing element $S_1$ for detecting the pressure at the measurement position $Q_1$ and the hollow chamber $4_1$ opening onto the measurement position are formed. This pressure sensing element $S_1$ is composed of a thin portion $5_1$ (of a thickness of roughly tens of μm) used as a diaphragm and a strain gauge $6_1$ formed on the surface of this thin portion $5_1$.

The pressure sensing element $S_1$ is formed according to a known semi-conductor etching method, and in particular, the strain gauge $6_1$ is formed from piezo-resistance elements (p-type resistance layers) formed by using selective diffusion of impurities (such as boron). When this strain gauge 6 becomes stressed, then its resistance value changes depending on the level of the stress.

In the same way, the pressure sensing elements $S_2-S_4$ are formed on the semi-conductor substrate 2, and there resistance values change in proportion to the pressures of the measurement positions $Q_2-Q_4$.

With the pressure sensor 10 according to the described composition, if pressure vibrations occur on the hemispherical surface of the elastic rubber body 1, said pressure vibrations propagate through the elastic rubber body as elastic waves and set up vibrations at the measurement position Q, and generates pressure vibrations inside the hollow chamber 4. In this case, the strain gauge 6 is stressed by the pressure difference between the interior pressure of the hollow chamber 4 and the exterior pressure coming through the atmospheric pressure release port 7, and its resistance value changes depending on said pressure vibrations.

On both sides of the strain gauges $6_1-6_4$, aluminum electrodes (not shown) are vapor deposited in order to connect to outside circuitry, they are resistance/voltage converted by the circuitry to be explained, and said voltage is output as the measurement voltage $V_1$ in proportion to the pressures at the measurement positions $Q_1-Q_4$.

Here, if necessary, it is possible not to have the hollow chambers $4_1-4_4$ be simply empty, but to fill them with a liquid with a low rate of heat expansion (such as water or alcohol), or a material of liquid form (such as gelatin). According to this, the vibrations generated at each of the measurement positions $Q_1-Q_4$ can be converted to measurement signals by the respective strain gauges $6_1-6_4$ with low rates of loss and more accuracy.

Figure 3:
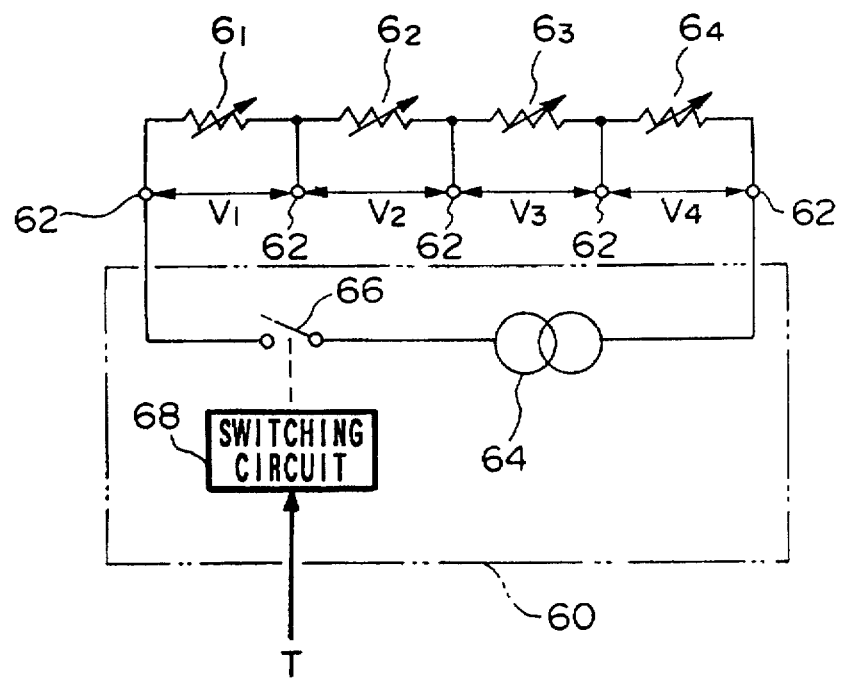
FIG. 3 is a block diagram showing the composition after adding the bias circuit 60 to the same pressure sensor 10.

Next, the electrical connections between the pressure sensing elements $S_1-S_4$ of the pressure sensor 10 and there bias will be explained with reference to FIGS. 3 and 4. In FIG. 3, the respective strain gauges $6_1-6_4$ are shown as variable resistors at the same value.

As shown in FIG. 3, the strain gauges $6_1-6_4$ corresponding to the respective pressure sensing elements $S_1-S_4$ are connected in series, and on both sides are provided the output electrodes 62.

Then, both ends of the strain gauges $6_1-6_4$ are connected to the bias circuit 60. This bias circuit 60 is composed from the constant current circuit 64, the switch 66 for turning "on/off" the output signal from this constant current circuit 64, and the switching circuit 68 for changing the switch 66 to "on" when the control signal T goes into the state "H". That is, when the control signal T goes into the state "H", the output signal of the constant current circuit 64 is marked onto the strain gauges $6_1-6_4$.

As stated above, the resistance value of the strain gauges changes with stress, and if the same constant current is run through each strain gauge $6_1-6_4$, then the voltages $V_1-V_4$ between each output electrode 62 will be proportionate to the respective pressures at the measurement positions $Q_1-Q_4$, and they will display the relative sizes of the respective pressures.

As waveform patterns for the control signal T, several types can be thought of depending on the design and use of the device for managing the output signal of the pressure sensor 10. For example, as control signals T, a signal 70 (see FIG. 4A) which is always in the "H" state regardless of whether it is during measurement or not during measurement, a pulse 72 (see FIG. 4B) which is in the "H" state off and on regardless of whether it is during measurement or not during measurement, a signal 74 (see FIG. 4C) which is in the "H" state during measurement, and a pulse 76 (see FIG. 4D) which is in the "H" state on and off during measurement (having a set duty ratio) can be chosen.

In this case, the time during measurement refers to the time periods for measuring pressure vibrations.

As a device for managing the output signal of the pressure sensor 10, if an accurate measurement is needed, then signal 70 is the most appropriate for the control signal T. On the other hand, if the spent energy needs to be minimized, then pulse signal 76 is the most appropriate for the control signal T. Furthermore, with this management device, if a compromise is to be made between measurement accuracy and energy use, then pulse signal 72 and signal 74 are appropriate.

This is due to the following reasons.

Since a constant current flows through the strain gauges $6_1-6_4$, some heat is generated. Because of this, there is a temperature difference between the times when he bias is set and when it is not, there is a slight difference in the resistance values due to this temperature difference, and this becomes a source of errors during the pressure measurement. If signal 70 is used as the control signal T, a constant current is sent through the strain gauges $6_1-6_4$ even during the times when a measurement is not being made, so if the pressure is measured after a set period of time has elapsed and the heat generation reaches equilibrium, then measurement errors due to temperature differences can be made extremely rare.

On the other hand, if pulse signal 76 is used as the control signal T, the constant current is sent to the strain gauges $6_1-6_4$ only during the time of measurement, and heat generation due to the current is suppressed, while it contributes to the low expenditure of energy. In this case, if the respective parts (A/D convertors, amplifiers, and such) of the measurement signal management device of the pressure sensor are operated simultaneously with the pulse signal 76, then it is possible to decrease further the expenditure of energy. Preferably, electricity should be sent through these parts only when the pulse signal 76 is in the "H" state.

Additionally, as a constant current bias, a composition is also possible in which the constant current circuit 64 outputs a constant current pulse (see FIG. 4E) having an interval sufficiently shorter than the pulse signal 72 or 76. In this case, it is of course also possible to combine together the signals 70, 72, 74, or 76 as the control signal T. In particular, if pulse signal 76 is used, the bias at the strain gauges $6_1-6_4$, as shown in FIG. 4F, becomes set for an extremely short time, and it is possible to make the heat expenditure extremely low. In this case as well, by operating the respective parts of the measurement signal management device of the pressure sensor 10 simultaneously with the constant current pulse, it becomes possible to lower the amount of heat expenditure. Furthermore, if electricity is sent through these parts only while the bias is set, then the amount of energy expenditure becomes extremely small.

While the interval of the bias signal must be short enough to respond to the changes in the pressure vibrations (satisfying the sampling theorem), it must be within the range manageable by the output device.

Furthermore, it is desirable that the pressure sensing elements $S_1-S_4$ be formed on the same semi-conductor substrate 2. This is because with semi-conductor manufacturing technology, it is easy to form and position elements on a single body, and rather than forming and positioning the pressure sensing elements one by one, it makes more sense in terms of precision and production.

Figure 2:
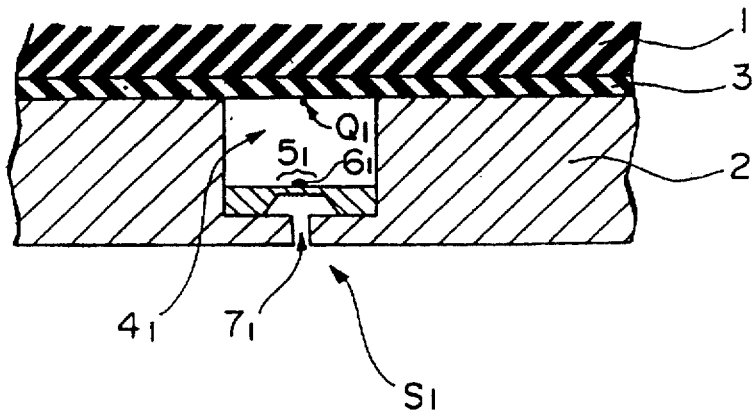
FIG. 2 is a cutaway diagram showing an enlarged view of the connecting portion between the elastic rubber body 1 and the semi-conductor substrate 2 of the same pressure sensor 10.
Figure 17A:
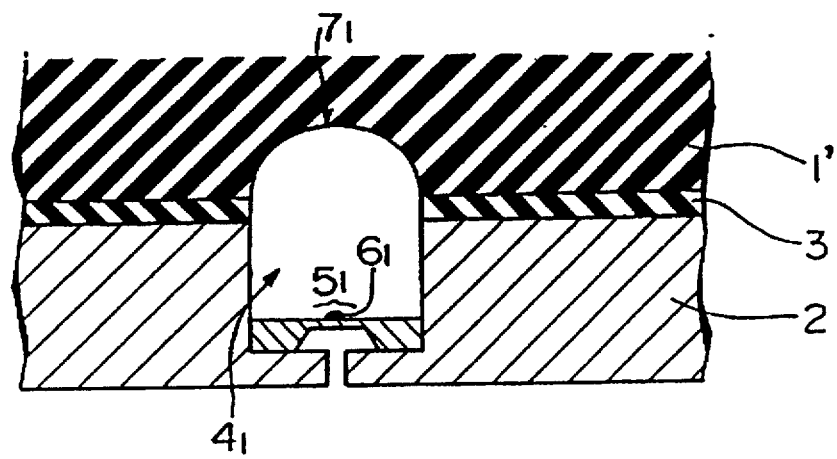
FIG. 17A is an enlarged cutaway diagram of the connecting portion between the elastic rubber body 1' provided with a dome-shaped cavity and the semi-conductor substrate 2.
Figure 17B:
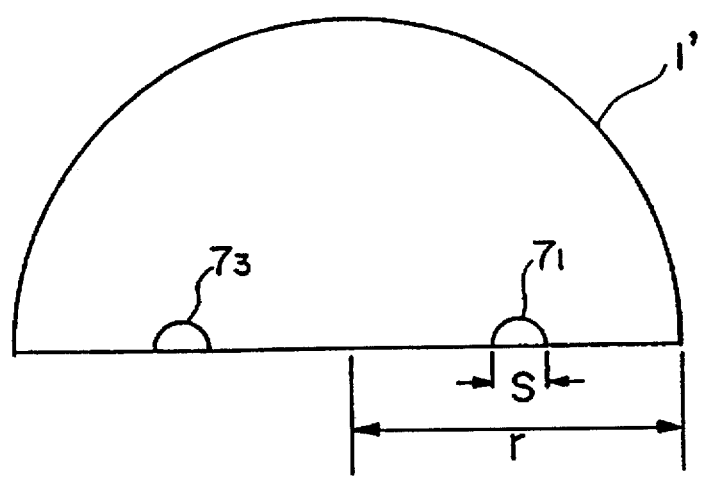
FIG. 17B is a cutaway diagram showing the relative sizes of the elastic rubber body 1' and the dome-shaped cavity 7.

Additionally, it is possible to provide a dome-shaped cavity at the positions corresponding to the pressure sensing elements $S_1-S_4$ on the elastic rubber body 1 (see FIG. 1) explained above. FIG. 17A shows an example of this, in which dome-shaped cavities $7_1-7_4$ are provided at the positions contacting the hollow chambers $4_1-4_4$ of the elastic rubber body 1 explained in FIG. 2. FIG. 17B is a cutaway diagram of the elastic rubber body 1' provided with the abovementioned dome-shaped cavities $7_1-7_4$. In the diagram, r is the radius of the bottom surface of the elastic rubber body 1', and s is the diameter of each of the dome-shaped cavities $7_1-7_4$. Additionally, the radius r of the elastic rubber body 1' and the diameter s of the dome-shaped cavities $7_1-7_4$ are set so as to satisfy the following equation:

$$\frac{4}{5} \geq \frac{s}{r} \geq \frac{1}{5} \tag{10}$$

By providing dome-shaped cavities $7_1-7_4$ such as these, the volumes of the spaces formed by the cavities $7_1-7_4$ and the hollow chambers $4_1-4_4$ become easily changeable due to the application of pressure at the elastic rubber body 1', and the pressure is easily converted to stress at the stress gauges 6, therefore, the overall sensitivity of the pressure sensor increases.

A-1-1: Pulse Detection Using the Pressure Sensor

Next, the principle of pulse detection using the pressure sensor 10 of the above composition will be explained. The arteries used as subjects for the present invention will mostly be those passing close to the skin.

Figure 5:
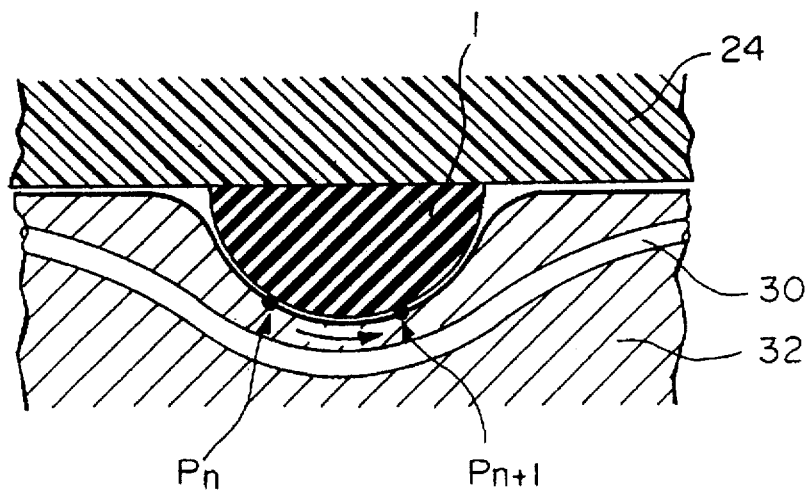
FIG. 5 is a cutaway diagram of the principal parts explaining the pulse measurement process of the same pressure sensor 10.

As shown in FIG. 5, we assume that the hemispherical face of the elastic rubber body 1 is pressed in the vicinity of the artery (here, the radial artery 30 for the sake of explanation). In this case, at the point $P_n$ on the hemispherical surface of the elastic rubber body, a pressure vibration is generated by the radial artery 30, that is, a vibration is created by a pulse. Here, the point $P_n$ is taken as the origin (center) of the vibration. This vibration propagates through the elastic rubber body 1, and is output as the electric signals representing the pulse by the pressure sensing elements $S_1$–$S_4$, that is, as measurement signals having the voltages $V_1$–$V_4$.

By running a time series procedure through the method described below on the voltages $V_1$–$V_4$ of the pressure sensing elements $S_1$–$S_4$, it is possible to determine the pulse front propagation speed, and the position of the artery.

A-1-2: Coordinate Calculation by the Pressure Sensor

Figure 6:
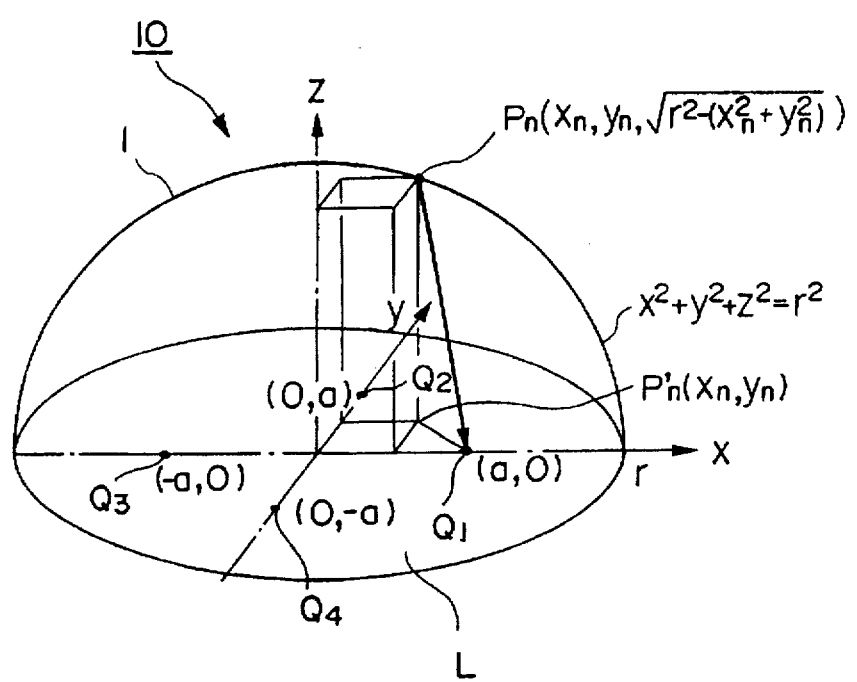
FIG. 6 is a simple oblique view diagram for explaining the position measurement process of the same pressure sensor 10.

Next, in order to explain the pulse front propagation speed measurement and the artery position measurement, the principle for calculating the coordinates of the pressure vibration point will be explained. FIG. 6 is an oblique view diagram for explaining the coordinate calculation principle, and in this diagram the pressure sensor 10 of FIG. 1 has been simplified for the sake of explanation.

When the hemispherical side of the elastic rubber body 1 is pressed in the vicinity of the artery so that the radial artery 30 is projected onto its bottom surface, at time t=n on the point $P_n$ on the hemispherical surface of the elastic rubber body 1, vibrations occur due to the pulse generated by the radial artery 30. These vibrations propagate through the elastic rubber body 1, attenuated as the square of the propagation distance, and are detected as measurement signals describing the pulse having voltages $V_1$–$V_4$ by the pressure sensing elements $S_1$–$S_4$.

The equation describing the spherical surface of the elastic rubber body 1 is as follows:

$$x^2+y^2+z^2=r^2 \qquad (1)$$

(wherein z>0)

Therefore, the coordinates (x, y, z) of an arbitrary point $P_n$ on the spherical surface of the elastic rubber body 1, taking the values of its x and y coordinates as $x_n$ and $y_n$, then Equation (1) can be rewritten as follows:

$$P_n(x_n, y_n, \sqrt{r^2-(x_n^2+y_n^2)}\,) \qquad (2)$$

Then, the distances between the point $P_n$ and the measurement positions $Q_1$–$Q_4$ of the pressure sensing elements $S_1$–$S_4$ may be expressed, with the use of Equation (2) and the Equation (p) which describes the coordinates of each measurement position, as follows:

$$\overline{P_nQ_1} = \sqrt{a^2-2ax_n+r^2} \qquad (3)$$

$$\overline{P_nQ_2} = \sqrt{a^2-2ay_n+r^2}$$

$$\overline{P_nQ_3} = \sqrt{a^2+2ax_n+r^2}$$

$$\overline{P_nQ_4} = \sqrt{a^2+2ay_n+r^2}$$

Next, since the vibrations which are generated at the point $P_n$ are attenuated as the square of the propagation distance through the elastic rubber body 1, the values of the voltages $V_1$–$V_4$ measured by the sensors have an inverse square relation with the distances between the point $P_n$ and the measurement positions of the corresponding sensors. Therefore, the following equations result:

$$V_1(\sqrt{a^2-2ax_n+r^2}\,)^2 = V_2(\sqrt{a^2-2ay_n+r^2}\,)^2 \qquad (4)$$
$$= V_3(\sqrt{a^2+2ax_n+r^2}\,)^2$$
$$= V_4(\sqrt{a^2+2ay_n+r^2}\,)^2$$

Then, from Equation (4), the values $x_n$ and $y_n$ of the x and y coordinates of the point $P_n$ become as follows:

$$x_n = \frac{(V_1-V_3)\cdot(a^2+r^2)}{2a(V_1+V_3)} \qquad (5)$$

$$y_n = \frac{(V_2-V_4)\cdot(a^2+r^2)}{2a(V_2+V_4)}$$

In this way, at the point $P_n$ on the hemispherical surface of the elastic rubber body 1, when pressure vibrations occur due to the pulse, it is possible to determine the coordinate values $x_n$ and $y_n$ of the point $P_n$ from the measurement voltages $V_1$–$V_4$ of the pressure sensing elements $S_1$–$S_4$. This is equivalent to determining the coordinates of the point $P_n'$ (see FIG. 6) which is the right angle projection of the point $P_n$ onto the plane of the measurement positions of the pressure sensing elements $S_1$–$S_4$ (the x-y plane), that is, the bottom surface L of the elastic rubber body 1.

In Equation (5), it is possible to individually determine the coordinate value $x_n$ from the voltages $V_1$ and $V_3$ of the pressure sensing elements $S_1$ and $S_3$ positioned on the x-axis and the coordinate value $y_n$ from the voltages $V_2$ and $V_4$ of the pressure sensing elements $S_2$ and $S_4$ positioned on the y-axis, so mutual influences on the calculation of the coordinates are avoided.

As can be seen on careful inspection of Equation (4), only the voltages of three of the pressure sensing elements $S_1$–$S_4$ are necessary in order to determine the coordinate values $x_n$ and $y_n$, but in such a case, the calculation of one of the coordinate values influences the other coordinate value.

For example, in order to calculate the coordinate values $x_n$ and $y_n$ with only $S_1$–$S_3$, first, the coordinate value $x_n$ can be calculated using $V_1$ and $V_3$, then, if this coordinate value $x_n$ is used in Equation (4), it is possible to calculate the coordinate value $y_n$ from the voltage $V_2$, but such a coordinate value $y_n$ would depend on the voltages $V_1$–$V_3$, so if there is a difference in the output characteristics of the pressure sensing elements, then an accurate coordinate calculation is not possible.

It is also possible to rewrite Equation (5) as follows:

$$x_n = \frac{(a^2+r^2)}{2a}\cdot\frac{V_1-V_3}{V_1+V_3} = K\cdot\frac{V_1-V_3}{V_1+V_3} \qquad (5)'$$

$$y_n = \frac{(a^2+r^2)}{2a}\cdot\frac{V_2-V_4}{V_2+V_4} = K\cdot\frac{V_2-V_4}{V_2+V_4}$$

(wherein K is a constant)

Therefore, the two-dimensional coordinates $(x_n, y_n)$ of the vibration point $P_n$ can easily be determined from the ratios of the differences and sums of the output voltages $V_1$-$V_4$ of the pressure sensing elements $S_1$-$S_4$. Then, if the coordinates ($x_n$, $y_n$) are determined, then it is easy to determine the coordinate $z_n$ from the aforementioned Equation (1).

In this embodiment, for Equations (1)-(5) used to determine the coordinate values $x_n$ and $y_n$ of the point $P_n'$, it is assumed that the elastic rubber body 1 is a perfect hemisphere, that is, the shape is that of a sphere which has been cut along a plane which includes the center.

Figure 16A:
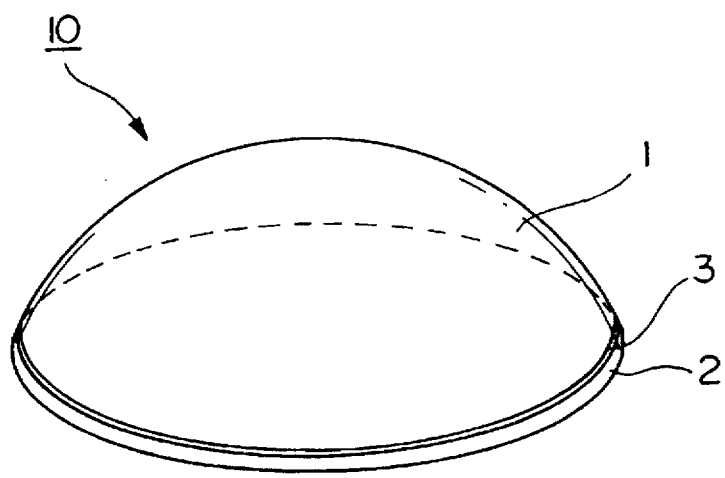
FIGS. 16A–16B are oblique view diagrams showing modified shapes for the pressure sensor 10.

However, when considering the sensations felt by the patient during attachment and use, the shape of the elastic rubber body 1, rather than the above hemisphere, should be of a shortened convex shape as shown in FIG. 16A.

Figure 16B:
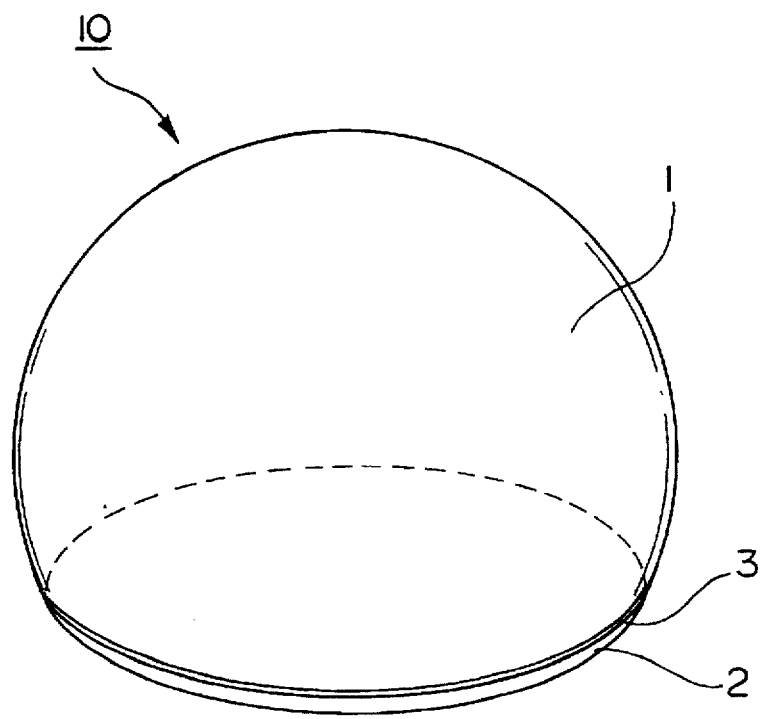

Additionally, from the standpoint of production, it is difficult to manufacture the pressure sensor 10 while meeting these requirements, and, as shown in FIGS. 16A and 16B (these diagrams show extreme examples), there are often deviations from the center of the sphere.

Even in such a case, if the amount of the deviation is within the allowable range to guarantee accuracy of the measurement, then it is possible to determine the coordinate values $x_n$ and $y_n$ by using Equation (5) as an approximation.

Here, this approximation will be explained. The shape of the elastic rubber body 1 will now be assumed to be an approximate hemisphere which has been cut from a perfect sphere at a distance of $\Delta z$ from the center.

In this case, the coordinates (x, y, z) of the measurement positions $Q_1$-$Q_4$ of the pressure sensing elements $S_1$-$S_4$, taking the radius of the elastic rubber body 1 as r and the origin as (0, 0, 0), are as follows:

$Q_1$ (a, 0, $\Delta z$)

$Q_2$ (0, a, $\Delta z$)

$Q_3$ (-a, 0, $\Delta z$)

$Q_4$ (0, -a, $\Delta z$)

As a result, the squares of the distances from the point $P_n$ to the measurement positions $Q_1$-$Q_4$ can be determined in a manner similar to that of Equation (3), and they will become as follows:

$$\overline{P_nQ_1}^2 = (x_n - \alpha)^2 + y_n^2 + (z_n - \Delta z)^2$$

$$\overline{P_nQ_2}^2 = x_n^2 + (y_n - \alpha)^2 + (z_n - \Delta z)^2 \tag{6}$$

$$\overline{P_nQ_3}^2 = (x_n + \alpha)^2 + y_n^2 + (z_n - \Delta z)^2$$

$$\overline{P_nQ_4}^2 = x_n^2 + (y_n + \alpha)^2 + (z_n - \Delta z)^2$$

provided that in these equations, $$z_n = \sqrt{r^2 - (x_n^2 + y_n^2)} \tag{7}$$

In this case as well, because the vibrations which are generated at the point $P_n$ are attenuated as the square of the propagation distance through the elastic rubber body 1, the values of the voltages $V_1$-$V_4$ measured at the sensors has an inverse square relation with the distances between the point $P_n$ and the measurement positions of the corresponding sensors. Therefore, the products of the squares of the respective distances in Equation (6) and the relevant output voltages $V_1$-$V_4$ are equal, and the values $x_n$ and $y_n$ of the x and y coordinates of the $P_n$ become as follows:

$$x_n = \frac{(V_1 - V_3) \cdot (a^2 + r^2 - 2z_n \cdot \Delta z + (\Delta z)^2)}{2a(V_1 + V_3)} \tag{8}$$

-continued
$$y_n = \frac{(V_2 - V_4) \cdot (a^2 + r^2 - 2z_n \cdot \Delta z + (\Delta z)^2)}{2a(V_2 + V_4)}$$

In Equation (8), $(\Delta z)^2$ may be ignored if ($\Delta z$) is sufficiently small in the z-axis direction.

Furthermore, as can be seen upon inspection of Equation (8), ($z_n \cdot \Delta z$) may be ignored if the distance a from the origin to the sensor is made as large as possible within the range of the radius r.

With this, Equation (8) becomes in effect equal to Equation (5).

Also in this embodiment, in order to determine the coordinates $x_n$ and $y_n$ of the point $P_n'$, the voltages $V_1$-$V_4$ of the output signals were entered into Equation (5), but they may be determined by the following method as well.

That is, some standard vibrations are set up on the exposed surface of the elastic rubber body 1, the relationship between the coordinates where the vibrations were generated and the ratios of the voltages $V_1$-$V_4$ are determined beforehand, and a table is prepared which shows this relationship.

In practice, in order to determine the coordinate values $x_n$ and $y_n$ of the point $P_n'$, it is possible to read the coordinates corresponding to the ratios of the voltages $V_1$-$V_4$ from this table.

In this way, it becomes unnecessary for the elastic rubber body 1 to be of a hemispherical form, it becomes sufficient to use a convex shape which is easily pressed onto the measurement surface.

A-1-3: The Calculation of the Shift Vector Component Due to the Pressure Sensor

Next, at the time t=n+1 (that is, after a single period of the sampling clock), suppose that the point of generation of the pressure vibrations has shifted to the point $P_{n+1}$ as a result of the propagation of the pulse front through the radial artery 30. In this case also, the coordinate values $x_{n+1}$ and $y_{n+1}$ of the point $P_{n+1}'$, which is the projection of the point $P_{n+1}$ onto the plane L, are determined.

Next, in a similar manner, the coordinate values of the points $P_{n+2}'$, $P_{n+3}'$, . . . at the times t=n+2, n+3, . . . are determined.

Because the pressure vibration source on the hemispherical shifts with the propagation of the pulse front through the radial artery 30, by tying together the points of the pressure vibration sources by the coordinate values of their right angle projections onto the plane L, the position of the radial artery 30 is described with respect to the plane L.

Furthermore, by subtracting the coordinate values determined in the previous period of the sampling clock from the determined coordinate values, that is, by determining the following:

$x_{n+1} - x_n$ $y_{n+1} - y_n$ it is possible to determine the x and y components of the vector describing the shift in blood flow in the artery over a single sampling period. Additionally, by determining the size of these components, that is, the shift distances, and dividing by the period of the sampling clock, it is possible to calculate the speed of the shift vector at the time of the sample, or equivalently, the pulse front propagation speed. The equation to determine this pulse front propagation speed, taking the frequency of the sampling clock as Fs, may be written as follows:

$$V = \frac{\sqrt{(x_{n+1}-x_n)^2 + (y_{n+1}-y_n)^2}}{\frac{1}{Fs}} \qquad (9)$$

A-2: Further Embodiments of the Pressure Sensor
<Embodiment 2>

Figure 7A:
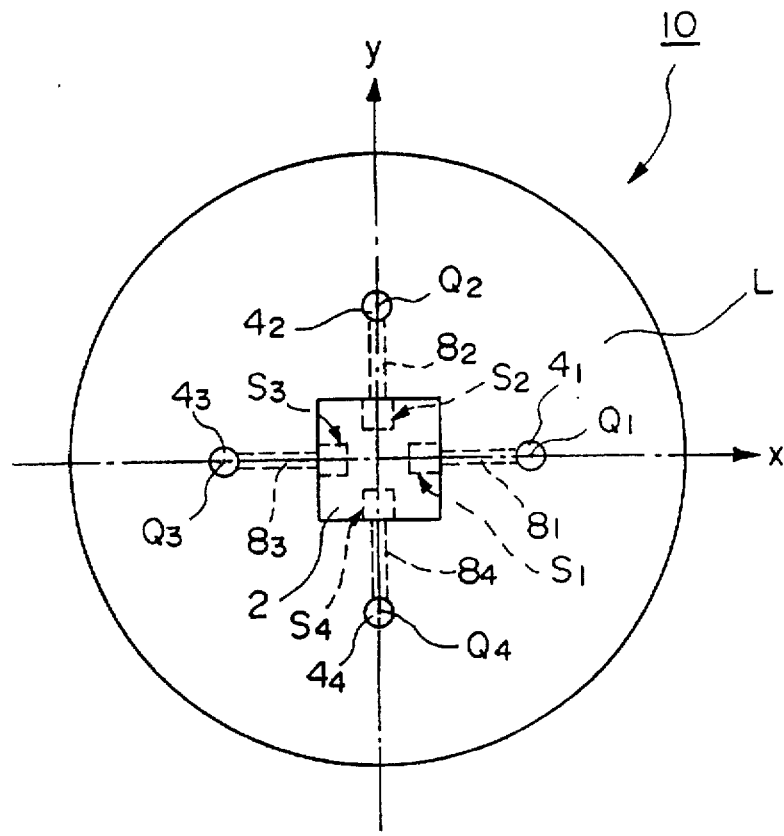
FIG. 7A is a plane diagram showing the composition of the pressure sensor 10 according to Embodiment 2 of the present invention.
Figure 7B:
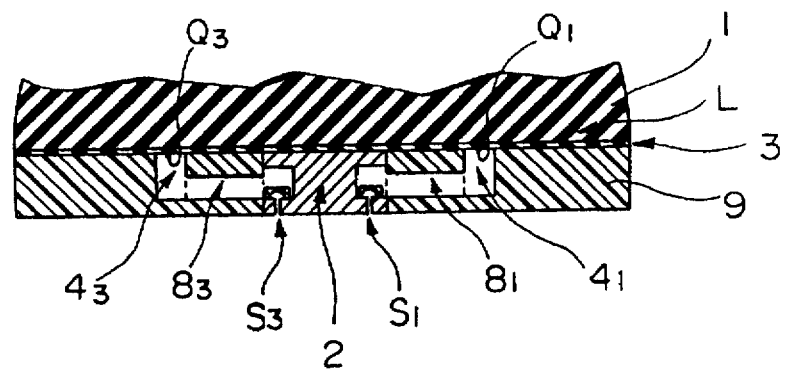
FIG. 7B is an enlarged cutaway view diagram showing the composition of the connecting portion between the elastic rubber body 1 and the semi-conductor substrate 2 according to the same embodiment.

Next, the pressure sensor according to the Embodiment 2 will be explained. FIG. 7A is a simple planar diagram for explaining the composition of this embodiment, and FIG. 7B is a cutaway diagram seen along the x axis in FIG. 7A. In these diagrams, for the parts which are the some as in FIGS. 1 and 2, the same reference numbers have been given, and their explanation will be omitted.

As shown in these diagrams, in the pressure sensor 10, a hollow chamber 41 has been provided which opens onto the measurement position $Q_1$, and furthermore, a hollow tube $8_1$ which opens onto the side wall of the hollow chamber $4_1$ stretches in the direction of the center of the surface L, and is connected to the semi-conductor substrate 2. In a similar manner, hollow chambers $4_2$–$4_4$ are also provided at the measurement positions $Q_2$–$Q_4$, and the hollow tubes $8_2$–$8_4$ stretch in the direction of the center of the surface L. On the semi-conductor substrate 2, the pressure sensing elements $S_1$–$S_4$ are provided, and are connected to the ends of the hollow tubes $8_1$–$8_4$ which stretch in the four directions.

In this case, it is preferable to make the hollow chamber $4_1$–$4_4$ and the hollow tubes $8_1$–$8_4$ separately from the semiconductor substrate 2, such as by forming them from a rigid body 9 composed of a hard plastic or metal. This way, it is possible to form the pressure sensing elements $S_1$–$S_4$ concentrated at the semiconductor substrate 2 without considering the measurement positions $Q_1$–$Q_4$, so there is the advantage that in the same amount of area, the number of pressure sensing elements can be increased, allowing the cost to be decreased.

Furthermore, with this Embodiment 2, it is also possible to fill the hollow chambers $4_1$–$4_4$ and the hollow tubes $8_1$–$8_4$ with a liquid with a low rate of heat expansion or a liquid form substance.

As the pressure sensor 10, it is also possible to directly attach distortion gauges to the measurement positions $Q_1$–$Q_4$ on the bottom surface L and measure the distortion due to the vibrations at said positions, but since with this composition distortion appears due to minor changes while the elastic rubber body is being pressed down, a composition in which the measurement of the pressure waves is made through an attachment layer 3 and a hollow chamber 4 is preferable.

Additionally, the number of pressure sensing elements was "4" in the above embodiment, but as stated above, it is also possible to have only "3". It is satisfactory as long as the measurement positions of the pressure sensing elements are on the bottom surface of the hemisphere so that the distances from the measurement positions of the pressure sensing elements to the points on the hemispherical surface of the elastic rubber body are able to be specified.

With the pressure sensor 10 according to the above Embodiments 1 and 2, the elastic waves due to the vibrations at the point $P_n$ propagate, not only in the directions of the measurement positions $Q_1$–$Q_4$, but in approximately all of the directions through the elastic rubber body 1. For this reason, the pressures generated at the measurement positions $Q_1$–$Q_4$ become small in comparison to the size of the vibrations generated at the point $P_n$, and there is a tendency for the voltage values $V_1$–$V_4$ to become correspondingly smaller. Therefore, with these embodiments, there is the disadvantage that the S/N ratio is easily lowered.

Embodiments 3 and 4, which improve on the S/N ratio, will now be explained.

<Embodiment 3>

Figure 8:
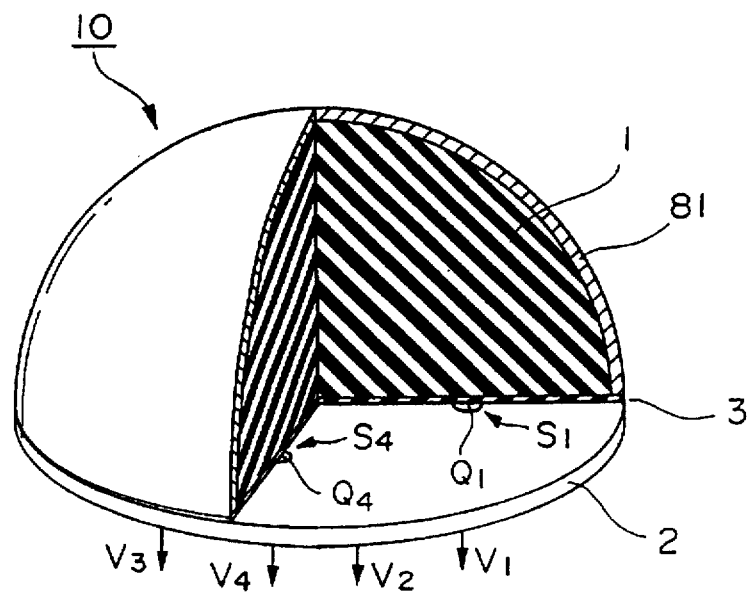
FIG. 8 is a partly cutaway oblique view diagram of the composition of the pressure sensor 10 according to Embodiment 3 of the present invention.

The present inventors have experimentally confirmed that if a material 81 (for example, hard plastic or metal) having a higher elasticity than the elastic rubber body 1 is coated onto the hemispherical surface of the elastic rubber body 1 as shown in FIG. 8, the output voltages $V_1$–$V_4$ resulting from the pressure sensing elements $S_1$–$S_4$ become comparatively large.

This is due to the fact that the surface elastic waves propagating along the surface of the hemisphere are hindered by the existence of the material 81, forcing them towards the direction of the center of the elastic rubber body, which then contributes to increases in pressure at the measurement positions $Q_1$–$Q_4$, and therefore to increases in the output voltages of the pressure sensing elements. In other words, the transmission coefficient describing the propagation of the elastic waves from the hemispherical surface to the measurement positions has improved.

Furthermore, with this embodiment, there is the advantage that, due to the coating of the material 81, the elastic rubber body 1 does not directly contact the patient, so decreases in the performance of the elastic rubber body 1 due to oil on the skin of the patient may be avoided.

<Embodiment 4>

Figure 9:
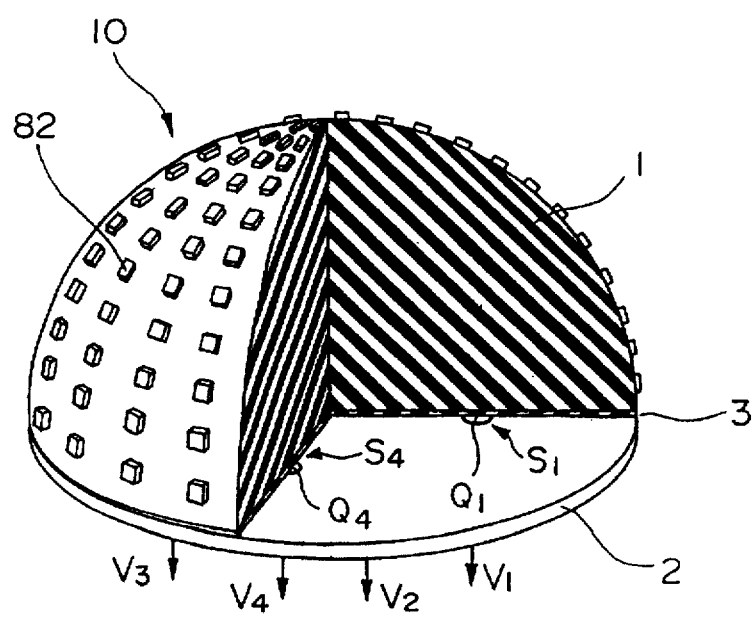
FIG. 9 is a partly cutaway oblique view diagram of the composition of the pressure sensor 10 according to Embodiment 4 of the present invention.

Additionally, as shown in FIG. 9, it is also possible to provide a scattering of fragments 82 of the material 81 on the hemispherical surface of the elastic rubber body 1. The fragments 82 may either be set into the hemispherical surface, or attached (the diagram shows an example in which they are attached).

At this time, regarding the transmission coefficient of the elastic waves mentioned above, those which travel to the measurement positions from the fragments 82 are improved more than those which travel to the measurement positions from the exposed surface of the elastic rubber body 1, so the vibration point $P_n$ on the hemispherical surface is automatically selected at a position where a fragment 82 has been set. Because of this, there is a problem in that the coordinate values of $P_n$ become scattered over all of the points which are the projections of the positions of the fragments 82 on the bottom surface L, but since the output voltages $V_1$–$V_4$ of the pressure sensing elements $S_1$–$S_4$ are increased, it is ultimately advantageous for the measurement of the pulse.

Furthermore, this problem can be overcome with the efficient placement of a large number of the fragments 82.

B: Pulse Management (Pulse Measurement, Pulse Front Propagation Speed Measurement, and Artery Position Display) Apparatus Next, an embodiment of a pulse management apparatus containing the pressure sensor 10 described above will be explained. This pulse management apparatus is to be built into a normal (for time display) watch, and with the output signal from the pressure sensor 10, performs pulse measurement, pulse front propagation speed measurement, and artery position display.

B-1: Outward Composition of the Pulse Management Apparatus

Figure 10:
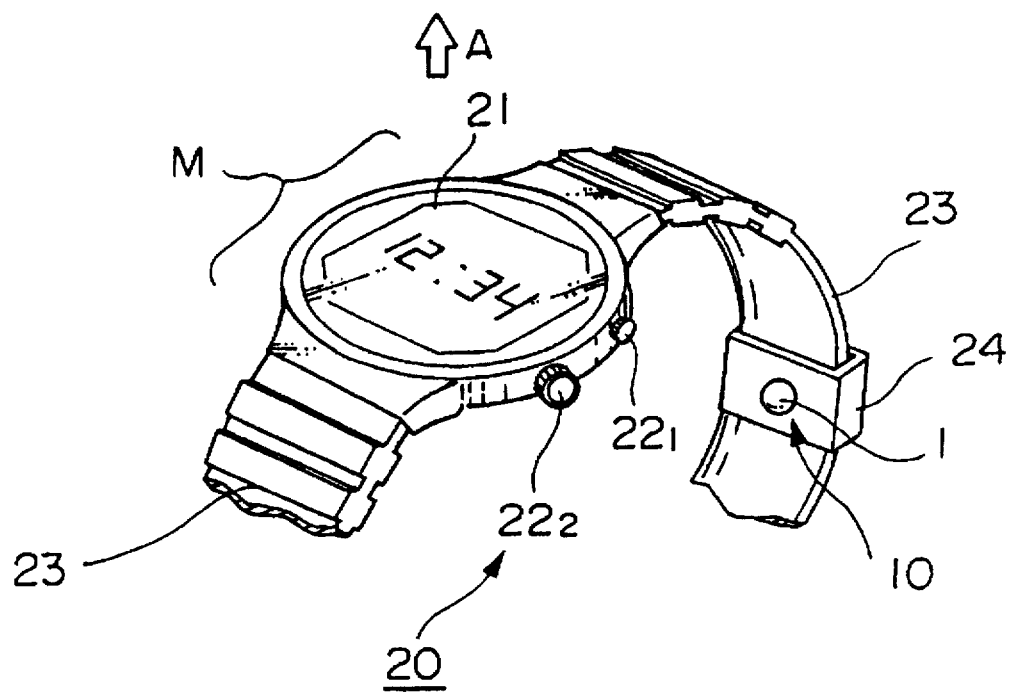
FIG. 10 is an oblique view diagram showing the outward composition of a wristwatch 20 equipped with the pulse management apparatus using the pressure sensor 10.

FIG. 10 is an oblique view diagram of the outward composition of the pulse management apparatus. As shown in this diagram, on the face M of the wristwatch 20, a dot-matrix form liquid crystal display panel 21 is provided, which displays such information as the present time and the position of the radial artery. In this diagram, A shows the direction of view of the liquid crystal display panel 21.

Additionally, on the right side of the watch face M, the switches $22_1$ and $22_2$ are provided, and by pressing these switches either one at a time or simultaneously, functions may be selected or various settings may be performed.

Furthermore, there is a pair of bands 23, and on the inner side of the buckle 24 on one of the bands 23, the elastic rubber body 1 of the pressure sensor 10 protrudes, and the band 23 having the buckle 24 is composed of a FPC (flexible printed circuit) board for delivering the output signals from the pressure sensor 10, coated with a soft plastic.

B-2: Electrical Composition of the Pulse Management Apparatus

Next, the electrical composition of this pulse management apparatus will be explained with reference to FIG. 11.

In the diagram, 11 is an A/D converter, which samples according to the timing of a clock CLK and A/D converts the measurement voltages $V_1$-$V_4$ of the pressure sensing elements $S_1$-$S_4$. In more detail, this A/D converter 11 sample holds the measurement voltages $V_1$-$V_4$ according to the timing of the clock CLK, and performs the A/D conversion by switching these voltages, in order, using a multiplexer at a sufficiently higher rate than the clock CLK. By this, although the number of voltages to be converted is "4" as in $V_1$-$V_4$, but only one A/D converter is required. Then, the converted voltages are delivered through an interface (not shown) and a bus to the CPU 12.

13 is a ROM, in which is stored programs for performing calculations by using the CPU 12, and tables showing the relationship between the pulse front propagation speed and the blood pressure value. 14 is a RAM, in which is stored various data calculation coordinates. 15 is a timer, which in addition to delivering the standard clock $\phi$ to the CPU 12, after the control signal S from the CPU 12, outputs the clock CLK by changing the period of the standard clock $\phi$.

16 is an LCD control circuit which, based on data delivered from the CPU 12 through the bus, generates a timing signal and display data for displaying on the liquid crystal display panel 21, and delivers them to the perpendicular control circuit 17 and the parallel control circuit 18. The perpendicular control circuit 17 and the parallel control circuit 18 are each connected to the electrodes of the liquid crystal display panel 21, and the perpendicular control circuit 17 controls the perpendicular electrodes, while the parallel control circuit controls the parallel electrodes. By these circuits, the display according to the data delivered from the CPU 12 is performed at the liquid crystal display panel 21.

25 is a switch interface which sends the set state of the switches $22_1$ and $22_2$ in FIG. 10 to the CPU 12.

The CPU 12 counts the standard clock $\phi$ and runs a known watch function, measures the pulse as a sample value for the voltages $V_1$-$V_4$, and when the pulse front propagation speed is measured or the artery position is displayed, the coordinate value $x_n$ and $y_n$ according to the Equation (5) is determined for each timing signal of the clock CLK.

Additionally, when the pulse front propagation speed is being measured or the artery position is being displayed, if the shift vector, that is, the shift speed, is greater than a set amount, then the CPU 12, according to a control signal S, orders the timer 15 to halve the period of the clock CLK, and if the shift speed is smaller, then the CPU 12, according to a control signal S, orders the timer 15 to double the period of the clock CLK.

The other tasks of the CPU 12 will be explained below. If a bias circuit 60 (see FIG. 3) is added to the pressure sensor 10, the clock CLK is sent to the bias circuit 60, and at the bias circuit 60, biases as the clock are set in the strain gauges $6_1$-$6_4$ with the same period as the clock CLK.

B-3: The Actions of the Pulse Management Apparatus

Figure 12A:
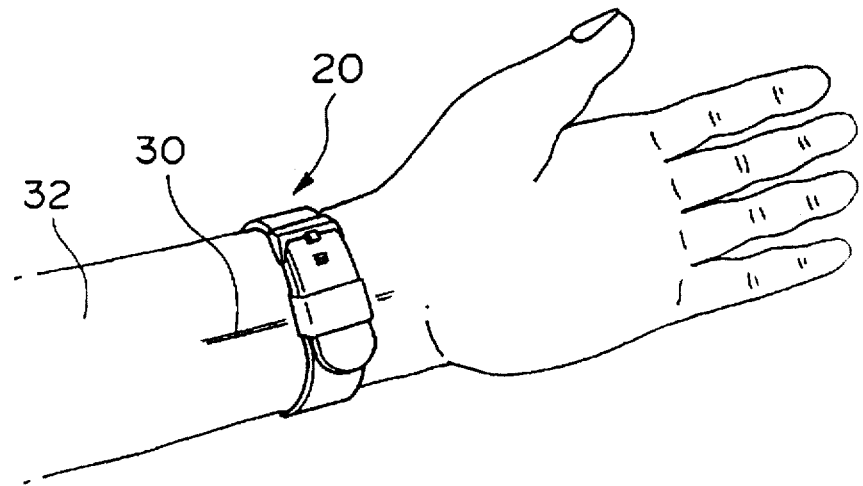
FIG. 12A is an oblique view diagram of the same wristwatch when worn.
Figure 12B:
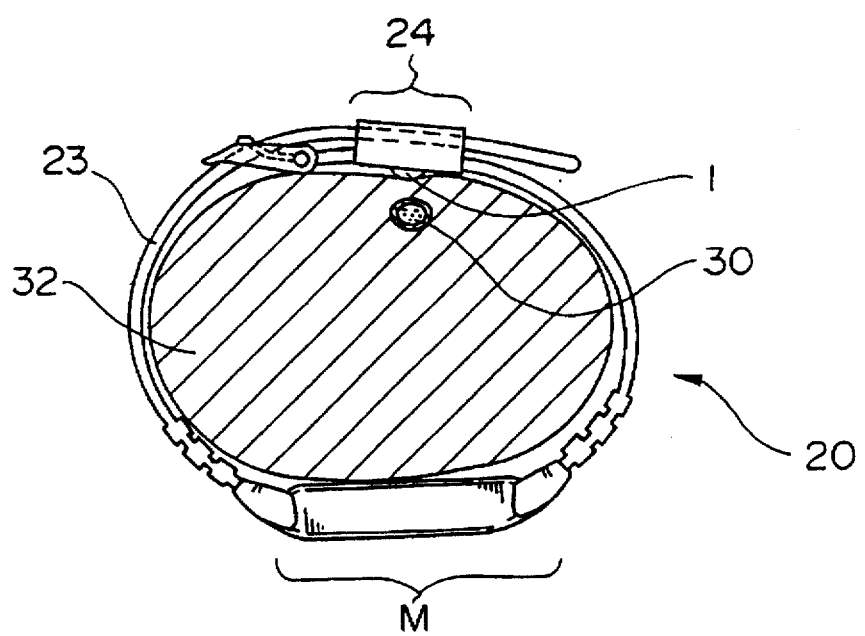
FIG. 12B is a cutaway diagram showing the same wristwatch when worn.

Next, the actions of the pulse management apparatus according to the above composition will be explained for each function. When the wristwatch 20 containing the pulse management apparatus is in use, as shown in FIGS. 12A and 12B, in order to position the elastic rubber body 1 provided on the buckle 24 in the vicinity of the radial artery 30, the wristwatch is strapped onto the patient's left wrist. This is the normal state of use of the wristwatch.

In this case, when the watch function is selected by the switches $22_1$ and $22_2$, the present time is displayed on the liquid crystal display panel 21. This watch display method is no different from those of the past, so its explanation will be omitted.

B-3-1: During Pulse Measurement

Next, the actions taking place during pulse measurement will be explained.

As mentioned above, when the elastic rubber body 1 is pressed in the vicinity of the patient's radial artery 30, blood flow changes in that artery, or the pulse, generates vibrations having the point $P_n$ on the hemispherical surface of the elastic rubber body 1 as the source. The vibrations propagate through the elastic rubber body 1 from the point $P_n$ to the measurement positions $Q_1$-$Q_4$, become pressure waves inside the hollow chambers $4_1$-$4_4$, are measured by the pressure sensing elements $S_1$-$S_4$ as the voltages $V_1$-$V_4$, and these voltages are then converted into digital signals. As a result, the pulse is converted into a scattered signal, and its analysis procedure is carried out by the CPU 12. In this case, it is not necessary to convert all of the voltages $V_1$-$V_4$ into digital values (only when the pulse waveform is being measured), it is possible for the CPU 12 to discriminate the one with the highest value, and convert only one (or more) of them.

Figure 13A:
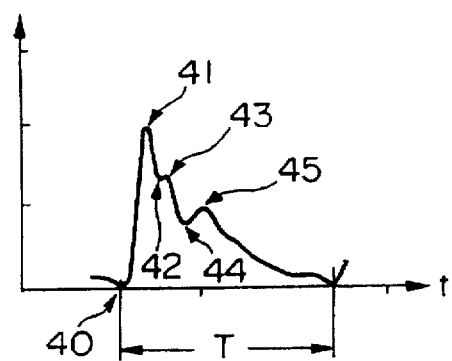
FIGS. 13A–13C are graphs showing normal pulse waveforms.
Figure 13B:
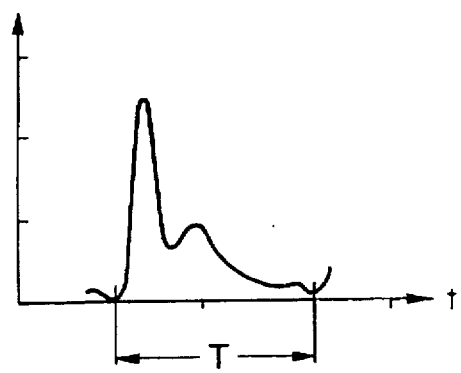
Figure 13C:
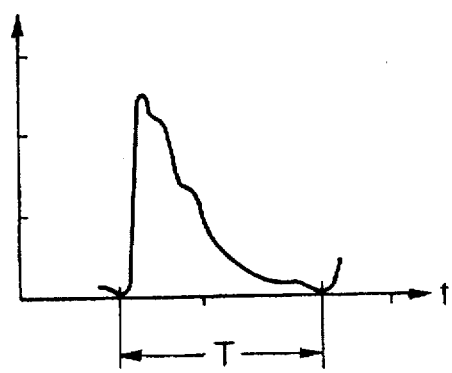

Here, the normal waveform for the pulse is shown in FIGS. 13A–13C. The pulse waveform may have various patterns depending on differences in the patients' physical condition and age, but all patterns have a minimum value 40 (absolute minimum) directly before the maximum value 41 (absolute maximum).

The CPU 12 takes the first and second derivatives of the measured pulse signal, and by regarding the signal changes in these differentiated signals, the mathematical coordinates for one period of the pulse signal are determined in order (in the order of minimum value 40, maximum value 41, second minimum value 42, second maximum value 43, third minimum value 44, and third maximum value 45). In a similar manner, the mathematical coordinates of the next period of the pulse signal are determined in order and are subtracted from the corresponding mathematical coordinates of the previous period, and the amounts of the differences and directions are calculated.

Afterwards, the CPU 12 repeats these actions, determining the trends in the mathematical coordinates of the pulse waveforms, and discriminates between the patients' physical and psychological information. Then, after this discrimination is made, it is displayed on the liquid crystal display panel 21.

Furthermore, it is possible to convert the voltages $V_1$-$V_4$ (one or more) into digital values, and choose the waveform, out of some pre-stored pulse waveforms corresponding to the patient's physical condition during times such as those of stress or pain, which most closely resembles the single cycle of the pulse waveform stored in the RAM 14, and thus determine the present condition of the patient.

As has been stated above, the information that is necessary from the pulse is, for the most part, the mathematical coordinates of the pulse waveform. According to this, then, if the pulse signal is simply sampled, a lot of unnecessary information is included. Furthermore, as is able to be seen from FIGS. 13A–13C, there is the problem that around the mathematical coordinates of the pulse waveform, the changes temporarily become more severe, requiring the setting of a high sampling rate, and thereby increasing the expenditure of energy. Specifically, when the composition is such that the pulse measurement apparatus is built into a wristwatch as in this embodiment, there is a limit to the capacity of the battery, so this problem is not able to be ignored.

Therefore, with this pulse measurement apparatus, when the minimum value 40 of the pulse waveform has been measured, then the delivery of electricity to the management circuit is begun, and while the maximum and minimum values are measured in order, after the last coordinate which is necessary (for example the third maximum 45 in FIG. 13A) has been measured, the delivery of electricity to the management circuit is stopped. Here, the management circuit refers to circuits other than those used for performing the pulse measurement and for keeping the time. In this case, the minimum value of the pule waveform can easily be measured if several periods of the pulse waveform are determined by normal sampling.

According to this composition, only the first half of each period of the pulse waveforms is effectively sampled, but all of the necessary information is able to be obtained, and there is the advantage that the energy expenditure decreases.

Furthermore, during this pulse measurement, it is possible to enter the sampled pulse signals in order into the RAM 14, and for example, fit the signal to the time axis and display a pulse waveform like those of FIG. 13 on the liquid crystal display panel 21. By storing the measured pulse signal in the RAM 14 in this way, various procedures become possible.

B-3-2: During Pulse Front Propagation Speed Measurement

Next, the actions will be explained for the case in which the function of measurement of the pulse front propagation speed has been chosen by the switches $22_1$ and $22_2$, and pressure is applied so as to project the artery onto the bottom surface L. As will be explained, this is because if the elastic rubber body 1 is pressed so far away from the artery so as not to allow the artery to be projected onto the bottom surface L, then the position of the artery is not able to be determined.

First, at time t=n, when the elastic rubber body 1 is pressed in the vicinity of the patient's radial artery 30, vibrations due to the pulse occur in the same manner as during pulse measurement, and elastic waves are generated in the elastic rubber body 1 as a result of these vibrations. These elastic waves are measured as pressure by the pressure sensing elements $S_1$–$S_4$, the coordinate values $x_n$ and $y_n$ of the projection of the coordinates of the vibration source onto the bottom surface L are calculated by the CPU 12 based on Equation (5), and are temporarily stored in the RAM 14.

Next, with the timing of the clock CLK at the time t=n+1, the CPU 12 determines the coordinate values $x_{n+1}$ and $y_{n+1}$ from Equation (5), storing the determined coordinate values in the RAM 14, and reading out the coordinate values $x_n$ and $y_n$. Then, using Equation (9), the pulse front propagation speed from the time t=n to t=n+1 is determined.

In the same way, at time t=n+2, the CPU 12 determines the coordinate values $x_{n+2}$ and $y_{n+2}$, stores them in the RAM 14, reads out the coordinate values $x_{n+1}$ and $y_{n+1}$, and determines the pulse front propagation speed from the time t=n+1 to time t=n+2.

Afterwards, the CPU 12 continually determines the pulse front propagation speed by repeating the same actions for each timing of the clock CLK.

As stated above, the blood pressure value and the propagation speed have a positive correlation, so by entering individual data (coefficient) which is specific to the patient, it is possible to determine the blood pressure value from the determined pulse front propagation speed. The individual data can be set in a menu format with on/off combinations of the switches $22_1$ and $22_2$.

Then, the determined pulse front propagation speed or the blood pressure value determined from the pulse front propagation speed can be displayed on the liquid crystal display panel 21.

B-3-3: During Artery Position Display

Next, the actions when the radial artery position display function is selected by the switches $22_1$ and $22_2$ will be explained, dividing them into the following two cases {1} and {2}.

{1} When the elastic rubber body 1 is pressed so that the artery is projected onto its bottom surface.

{2} When the elastic rubber body 1 is pressed so that the artery is not projected onto its bottom surface.

<In the case of {1}>

First, at time t=n, in the same manner as during the pulse measurement, vibrations due to the pulse occur on the hemispherical surface of the elastic rubber body 1, and an elastic wave is generated due to the vibrations. These elastic waves are detected as pressure by the pressure sensing elements $S_1$–$S_4$, the coordinate values $x_n$ and $y_n$ of the projection of the coordinates of the vibration source on the bottom surface L are calculated by the CPU 12 based on Equation (5), and are temporarily stored in the RAM 14.

Next, with the time t=n+1 as the timing on the clock CLK, the CPU 12 determines the coordinate values $x_{n+1}$ and $y_{n+1}$ from Equation (5), and stores them in the RAM 14.

Similarly below, for the clock timings t=n+2, n+3, . . . , the CPU 12 determines the coordinate values $(x_{n+2}, y_{n+2})$, $(x_{n+3}, y_{n+3})$ from Equation (5), and stores them in the RAM 14.

With this embodiment, it is possible to concentrate on the pressure waves corresponding to the maximum value 41 (see FIG. 13) of the pulse signal, and determine the coordinate shift of this pressure wave. In this case, the vibrations on the hemispherical surface of the elastic rubber body 1 are also maximized, and one of the voltages $V_1$–$V_4$ are maximized on the point $P_n$.

Therefore, because the effects of noise can be decreased, it is possible to perform the coordinate calculation accurately.

Figure 14:
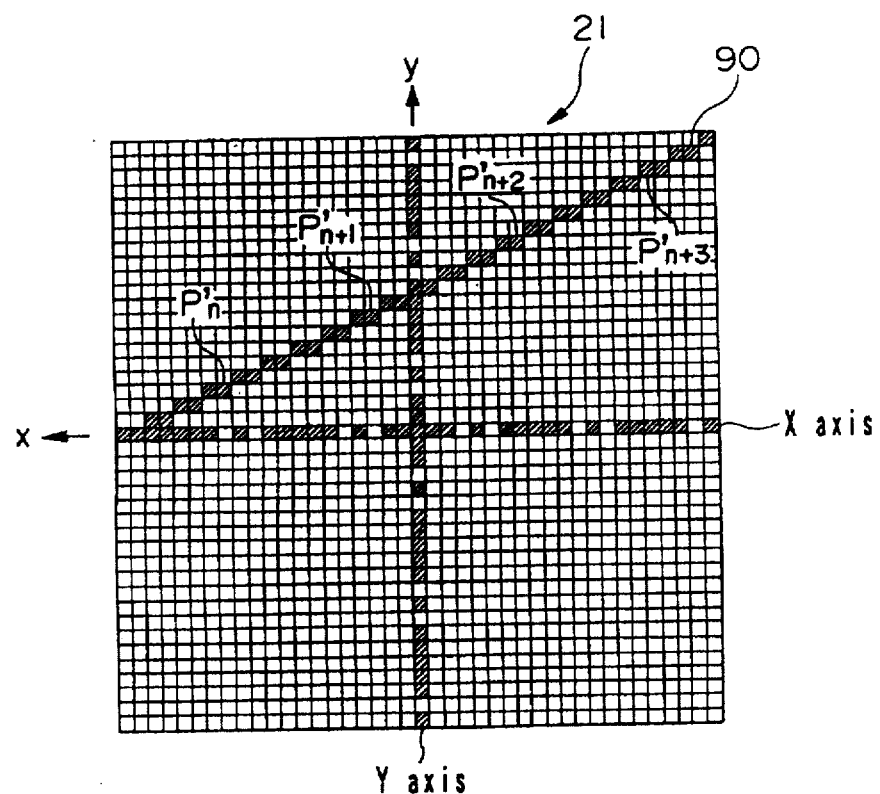
FIG. 14 is a plane diagram showing an example of a display from the liquid crystal display panel 21 of the same wristwatch 20.

Next, the CPU 12 measures approximately one period of the pulse signal by sampling of the voltages $V_1$–$V_4$, reads the coordinates $(x_{n+1}, y_{n+1})$, $(x_{n+2}, y_{n+2})$, $(x_{n+3}, y_{n+3})$, . . . from the RAM 14, determines the straight line 90 through these coordinates using a least squares fit, and displays the straight line on the liquid crystal display panel 21. An example of this type of display using the liquid crystal display panel 21 is shown in FIG. 14. Regarding this diagram, the reason the positive x-axis goes to the left is that the pressure sensor 10 has been pressed in the vicinity of the radial artery 30 from the state of FIG. 1, and been turned around.

As stated above, the vibration source which arises on the hemispherical surface of the elastic rubber body 1 shifts along the radial artery 30, so the straight line 90, which is the projection of the shift of the vibration source onto the bottom surface L displayed on the liquid crystal display panel 21, describes the radial artery 30.

In this case, by displaying the placement direction of the measurement positions $Q_1$–$Q_4$ on the liquid crystal display panel 21, that is, by displaying the x and y axes using dotted lines, it is possible to visually discriminate the positional relationship between the radial artery 30 and the pressure sensor 10.

If the radial artery 30 and either the x or y axis overlap, then the pressure sensor 10 is in a position to most accurately measure the pulse. If they are in such a positional relationship, for example, if the elastic rubber body is pressed so that the x-axis and the radial artery 30 overlap, the distance between the pressure sensing element $S_1$ ($S_3$) is as short as possible, and attenuation due to the elastic rubber body 1 is minimized. As a result, the voltage $V_1$ ($V_3$) of the measurement signal of the pressure sensing element $S_1$ ($S_3$) is maximized, and the effects of noise are able to be minimized.

Then, if the positional relation between the radial artery 30 and the pressure sensor 10 is able to be visually discriminated, the patient is able to reposition the pressure sensor 10 so as to optimize the positional relationship, and due to this, the pulse can be measured under he optimum conditions.

This is possible if the composition of the pressure sensor 10 is such that it is rotatable with respect to the buckle 24 (see FIG. 10).

<In the Case of {2}>

The radius r of the elastic rubber body 1 of this embodiment is approximately 2 mm, furthermore, with the present invention, the artery is assumed to pass near the surface layers of the patient's skin. Therefore, if the elastic rubber body 1 is pressed at a position away from the artery, then the point $P_n$, which is the vibration source of the pulse due to the artery, moves along the hemispherical surface (at a constant low latitude) near the bottom surface L of the elastic rubber body 1. If the coordinates thus calculated are tied together, then a curve results which is equal in length to the radius of the elastic rubber body 1. This contradicts the fact that the artery is an approximately straight line. Conversely, from this contradiction, it is possible to recognize that the artery has not been projected onto the bottom surface L.

With this artery position display apparatus, flit is recognized that the artery is not projected onto the bottom surface L of the elastic rubber body 1, then a caution to that effect, as well as the direction of the position of the artery at which pressure should be applied determined from the curve, are displayed by the liquid crystal display panel 21.

Additionally, the CPU 12 outputs a control signal S in accordance with the pulse front propagation speed V determined by Equation (9), and controls the frequency of the clock CLK in the timer 15.

That is, the CPU 12 recognizes in which of the following ranges the pulse front propagation speed lies:

$(0 \leq)$ $V < V_{MIN}$ ... ($\alpha$)

$V_{MIN} \leq V < V_{MAX}$ ... ($\beta$)

$V_{MAX} \leq V$ ... ($\gamma$)

Here, $V_{MIN}$ and $V_{MAX}$ are pre-set threshold values. Then, a control signal S is sent to the timer 15 such that, if the pulse front propagation speed V is in the range ($\alpha$) then the present clock CLK period is doubled, if the pulse front propagation speed V is in the range ($\beta$) then the present clock CLK period is maintained, and if the pulse front propagation speed V is in the range ($\gamma$) then the present clock CLK period is halved.

Due to this, with the present embodiment, a sampling rate appropriate to the pulse front propagation speed is chosen.

Additionally, with the abovementioned pulse management apparatus, differences in the output characteristics of the pressure sensing elements $S_1$–$S_4$ can be canceled with the following method. With this method, technology is used for determining the coordinate values of the point $P_n'$ from the previously mentioned three pressure sensing elements.

First, choosing three pressure sensing elements from the four, the coordinate values $x_n$ and $y_n$ are calculated from only these pressure sensing elements. Next a different combination of pressure sensing elements is chosen, and the coordinate values $x_n$ and $y_n$ are calculated. There are four possible combinations ($=_4C_3$) of three elements in a group of four, so with the remaining two combinations as well, the coordinate values $x_n$ and $y_n$ are calculated. If the output characteristics of all of the pressure sensing elements $S_1$–$S_4$ are identical, then the coordinate values $x_n$ and $y_n$ calculated independently according to these four combinations should mutually agree. If they do not agree, then it is safe to say that the output characteristics are different, and if the calculated coordinates are made to agree by modifying the measurement voltages from the calculated coordinates, then it is possible to cancel the mutual disagreement between the output characteristics resulting from individual differences between the pressure sensing elements, and thus obtain more accurate coordinate values.

Figure 15:
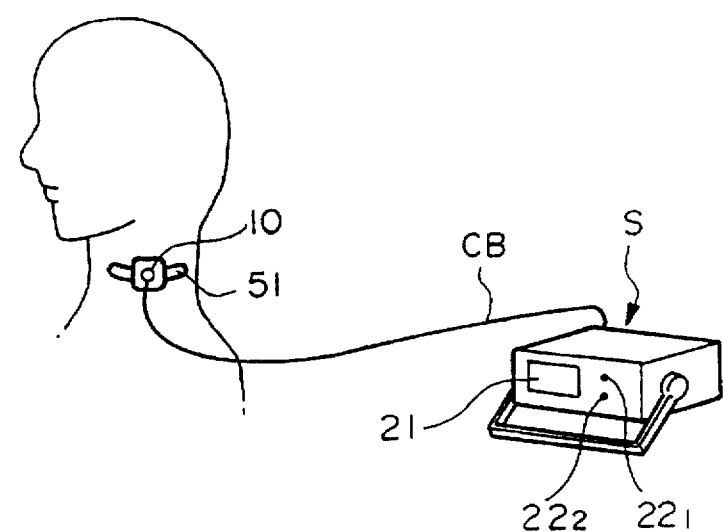
FIG. 15 is an oblique view diagram showing the composition of another embodiment of the pulse management apparatus.

This pulse management apparatus has a composition so as to measure the pulse of the radial artery by attaching it to a wristwatch, but of course the present invention is not limited to such a composition. That is, the composition does not necessarily be that of a wristwatch, and the composition may be such as to measure the pulse of a different artery. An example of such a composition is shown in FIG. 15.

Figure 11:
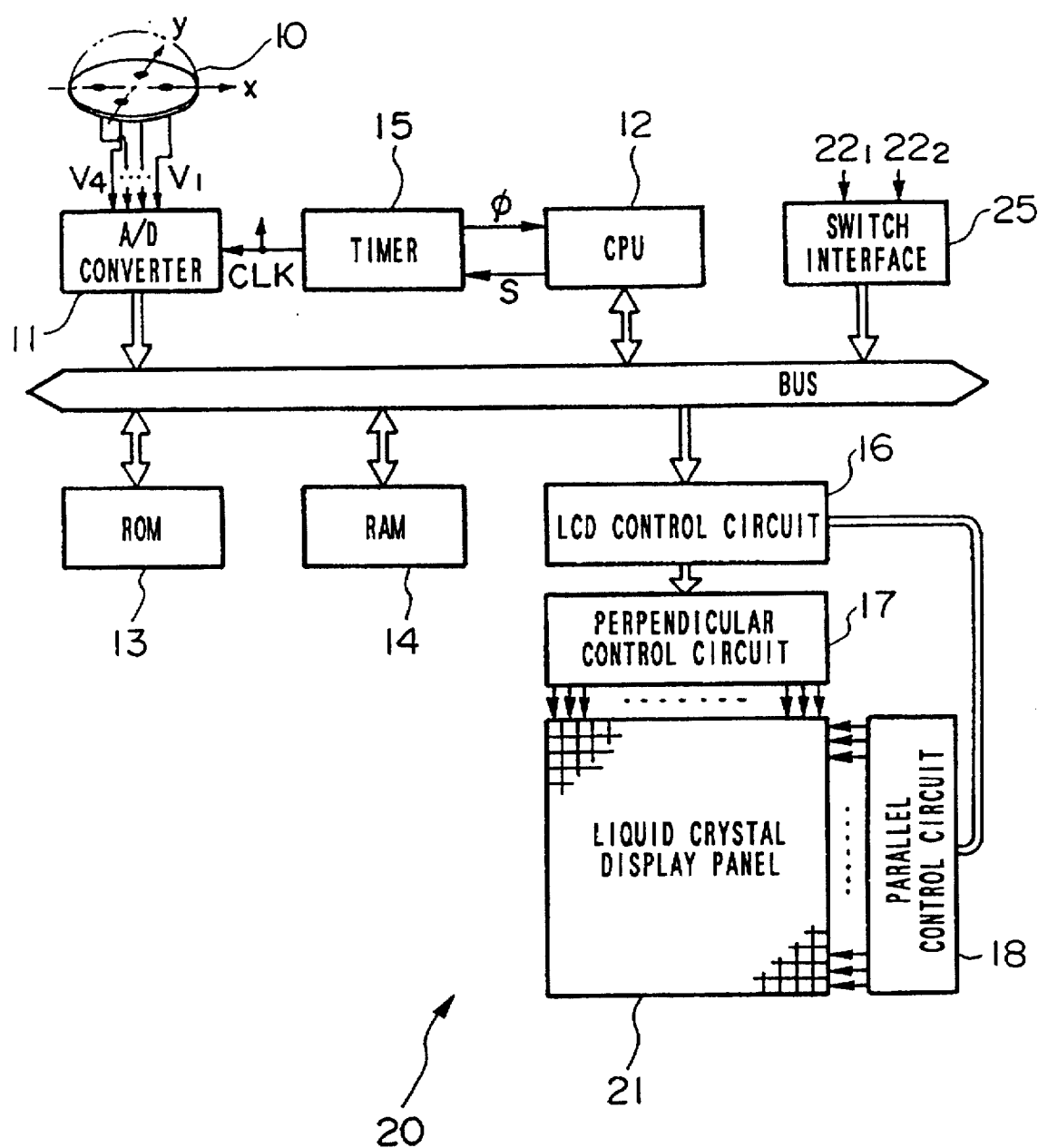
FIG. 11 is a block diagram showing the electrical composition of the same wristwatch 20.

In this example, the pressure sensor is pressed in the vicinity of the patient's carotid artery by the tape 51, and the measurement signal of the pressure sensor 10 is sent through the cable CB to the main body S, of which the electrical composition is shown in FIG. 11.

Furthermore, the pressure sensor according to the present invention is not limited to use on the pulse of patients, it can of course be used as a general pressure sensor for measuring pressure vibrations in any object.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A pressure sensing apparatus including:

a flat surface;

at least three pressure measurement means for measuring pressures at different measurement positions on said flat surface, and for outputting output signals proportional to pressures measured at said measurement positions;

an elastic member having a convex shape for propagating pressure vibrations and for attenuating said pressure vibrations as they propagate across said elastic member;

an attachment means for attaching said elastic member to said flat surface so that a bottom surface of said elastic member covers said measurement positions; and wherein said elastic member includes an exposed surface for engagement with a measurement surface whereby pressure vibrations on said measurement surface are measured by said at least three pressure measurement means in accordance with pressure vibrations propagated across and attenuated by said elastic member.

2. A pressure sensor according to claim 1, wherein said elastic member and said at least three pressure measurement means are attached by an adhesive layer having elasticity.

3. A pressure sensor according to claim 1, wherein the number of said at least three pressure measurement means is four, their measurement positions each lie on orthogonal axes which intersect at a center of the bottom surface of said elastic member, and are positioned at equal distances from said center of the bottom surface.

4. A pressure sensor according to claim 1, wherein said at least three pressure measurement means are formed on the some semiconductor substrate.

5. A pressure sensor according to claim 4, wherein underneath the bottom surface of said elastic member, hollow chambers are provided, each opening onto a different position on said flat surface, and each of said at least three pressure measurement means are stored in one of said hollow chambers, wherein they measure the internal pressures of said hollow chambers.

6. A pressure sensor according to claim 5, wherein each of said hollow chambers is filled with a liquid substance.

7. A pressure sensor according to claim 4, the bottom surface of said elastic member further including,
hollow chambers opening onto different positions on said flat surface, and
pressure transmission routes for guiding the internal pressures of said hollow chambers to each of said at least three pressure measurement means
and each of said at least three pressure measurement means measures the internal pressure of the corresponding pressure transmission route.

8. A pressure sensor according to claim 7, wherein each of said hollow chambers and said pressure transmission routes are filled with a liquid substance.

9. A pressure sensor according to claim 7, wherein said pressure transmission routes are composed of rigid bodies.

10. A pressure sensor according to claim 1, further including a highly elastic member having a higher elasticity than said elastic member is coated on an exposed surface of said elastic member.

11. A pressure sensor according to claim 1, further including fragments of a highly elastic material having a higher elasticity than said elastic member are distributed dispersively on an exposed surface of said elastic member.

12. A pressure sensor according to claim 1, wherein each of said at least three pressure measurement means outputs signals complying with the pressure by the setting of a set bias signal,
and having a bias signal setting means for setting an equal bias signal for each of said at least three pressure measurement means.

13. A pressure sensor according to claim 12, wherein said bias signal setting means only sends bias signals to each of said at least three pressure measurement means during pressure measurement.

14. A pressure sensor according to claim 12, wherein said bias signal setting means intermittently sends bias signals to each of said at least three pressure measurement means.

15. A pressure sensor according to claim 12, wherein said bias signal is a constant current pulse.

16. A pressure sensing apparatus according to claim 1 including a converter means for converting said output signals from said at least three pressure measurement means to digital signals.

17. A pressure vibration measurement apparatus using a pressure sensor according to claim 16, wherein said converter means performs conversions to digital signals when bias signals are being sent to said at least three pressure measurement means.

18. A pressure sensing apparatus according to claim 16 including a first memory means for storing at least one of the digital signals converted by said converter means.

19. A pressure sensing apparatus according to claim 16, wherein said measurement surface is an individual's skin and wherein a pulse from an artery in the vicinity of said elastic member in engagement with said measurement surface is measured as pressure vibrations by at least one of said at least three pressure measurement means.

20. A pressure sensing apparatus according to claim 19, including a strap for attaching said elastic member to a wrist of said individual.

21. A pressure sensing apparatus according to claim 19, further including:
a first calculation means for determining, after each passage of a set time interval, the coordinates of the projection on said flat surface of a pressure vibration point, generated on said exposed surface of said elastic member by a pulse from an artery in the vicinity of said elastic member, from ratios of measurement signals from said at least three pressure measurement means; and
a display means for plotting and displaying the coordinates determined after each passage of a set time interval by said first calculation means.

22. A pressure sensing apparatus according to claim 21, further including a time interval control means for changing the length of said time interval by discerning a size of a shift speed of said coordinates.

23. A pressure sensing apparatus according to claim 21, wherein said display means includes means for comparing and displaying measurement positions of said at least three measurement means and the coordinates determined by said first calculation means.

24. A pressure sensing apparatus according to claim 19, including a mathematical coordinate calculation means for calculating mathematical coordinates of a waveform of a pulse measured by at least one of said at least three pressure measurement means.

25. A pressure sensing apparatus according to claim 22, further including a discerning means for discerning a physical condition of said individual based on the mathematical coordinates calculated by said mathematical coordinate calculation means.

26. A pressure sensing apparatus according to claim 25, further including a first display means for displaying the physical condition of the patient discerned by said discerning means.

27. A pressure sensing apparatus according to claim 24, wherein said mathematical coordinate calculation means includes a pulse waveform mathematical coordinate calculation means for outputting a coordinate signal after measuring a minimum value of the pulse waveform and three maximal values subsequent to said minimum value.

28. A pressure sensing apparatus according to claim 19, further including:
a first calculation means for determining, after each passage of a set time interval, the coordinates of the projection on said flat surface of a pressure vibration point, generated on said exposed surface of said elastic member by a pulse from an artery in the vicinity of said elastic member, from ratios of measurement signals from said at least three pressure measurement means;

a second calculation means for determining a shift speed of the coordinates determined after each passage of a set time interval by said first calculation means; and means for outputting said shift speed as a pulse front propagation speed of said artery.

29. A pressuring sensing apparatus according to claim 28, further including a first time interval control means for changing the length of said set time interval by discerning the size of said shift speed.

30. A pressure sensing apparatus according to claim 28, further including:
- a memory means for pre-storing a correlation between a pulse front propagation speed and a normal blood pressure;
- a blood pressure value calculation means for reading an output pulse front propagation speed and correlating said speed with the set individual data in said memory to output a blood pressure value of said individual being monitored.

31. A pressure sensing apparatus according to claim 30, further including a second display means for displaying an individual's blood pressure information output by said blood pressure value calculation means.

32. A pressure sensor according to claim 1, wherein dome-shaped cavities are provided at positions covering the measurement positions of said pressure measurement means of said elastic member.

33. A pressure sensor according to claim 32, wherein, if the diameter of the bottom surface of said dome-shaped cavity is s, and the radius of the bottom surface of said elastic member is r, then said dome-shaped cavity is provided so as to satisfy the condition:

$$\frac{4}{5} \geq \frac{s}{r} \geq \frac{1}{5}.$$

* * * * *

UNITED STATES PATENT AND TRADEMARK OFFICE
CERTIFICATE OF CORRECTION

PATENT NO. : 5,704,363
DATED : January 6, 1998
INVENTOR(S) : Kazuhiko Amano

It is certified that errors appear in the above identified patent and that said Letters Patent is hereby corrected as shown below:

Title page, item number 56: Foreign Patent Documents, change Patent Document No. 2-246861 from "Japan" to --United Kingdom--.

Column 23, line 15, change "some" to --same--.

Column 24, line 44, change "claim 22" to --claim 24--.

Signed and Sealed this

Fifth Day of May, 1998

*Attest:*

BRUCE LEHMAN

*Attesting Officer*  *Commissioner of Patents and Trademarks*